US006384210B1

(12) United States Patent
Blanchard

(10) Patent No.: US 6,384,210 B1
(45) Date of Patent: May 7, 2002

(54) SOLVENT FOR BIOPOLYMER SYNTHESIS, SOLVENT MICRODROPLETS AND METHODS OF USE

(75) Inventor: Alan P. Blanchard, Kenmore, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/381,487

(22) PCT Filed: Mar. 20, 1998

(86) PCT No.: PCT/US98/05483

§ 371 Date: Mar. 13, 2000

§ 102(e) Date: Mar. 13, 2000

(87) PCT Pub. No.: WO98/41531

PCT Pub. Date: Sep. 24, 1998

Related U.S. Application Data

(63) Continuation-in-part of application No. 09/008,120, filed on Jan. 16, 1998, which is a continuation-in-part of application No. 08/821,156, filed on Mar. 20, 1997, now Pat. No. 6,028,189.

(51) Int. Cl.$^7$ ................... C07H 21/00; C07H 21/02; C07H 21/04; B01J 10/00; B41J 2/01

(52) U.S. Cl. .............. 536/25.3; 536/23.1; 536/24.3; 422/129; 422/131; 347/1; 347/7; 347/40; 347/85; 347/107

(58) Field of Search .................. 536/25.3, 23.1, 536/24.3; 422/129, 131; 347/1, 85, 7, 40, 107

(56) References Cited

U.S. PATENT DOCUMENTS

| | | | |
|---|---|---|---|
| 4,689,405 A | 8/1987 | Frank et al. | |
| 4,877,745 A | 10/1989 | Hayes et al. | |
| 4,940,760 A | 7/1990 | Boettcher et al. | |
| 5,047,524 A | 9/1991 | Andrus et al. | |
| 5,063,081 A | 11/1991 | Cozzette et al. | |
| 5,112,974 A | 5/1992 | Barton | |
| 5,124,444 A | 6/1992 | Van Ness et al. | |
| 5,130,369 A | 7/1992 | Hughes et al. | |
| 5,143,854 A | 9/1992 | Pirrung et al. | |
| 5,149,798 A | 9/1992 | Agrawal et al. | |

(List continued on next page.)

FOREIGN PATENT DOCUMENTS

| | | |
|---|---|---|
| FR | 2747692 | 10/1997 |
| JP | 59024244 A | 2/1984 |
| WO | WO 89/10977 | 11/1989 |
| WO | WO 90/00626 | 1/1990 |
| WO | WO 92/10588 | 6/1992 |
| WO | WO 93/17126 | 9/1993 |
| WO | WO 94/01215 | 1/1994 |
| WO | WO 94/27719 | 12/1994 |
| WO | WO 95/11748 | 5/1995 |
| WO | WO 95/25116 | 9/1995 |

(List continued on next page.)

OTHER PUBLICATIONS

Atkinson and Smith, "Solid Phase Synthesis of Oligodeoxyribonucleosides by the Phosphitetriester Method," *Oligonucleotide Synthesis*, M.J. Gait, ed., Oxford IRL Press, pp. 35–39 (1984).

Blackburn and Gait (eds), *Nucleic Acids in Chemistry and Biology*, Second Edition, New York: Oxford University Press (1996).

Blanchard and Hood, "Oligonucleotide Array Synthesis Using Ink Jets" Eighth International Genome Sequencing and Analysis Conference, TIGR Science Education Foundation, Inc. (Oct. 5–8, 1996).

Blanchard et al., "High–density oligonucleotide arrays," *Biosensors & Bioelectronics* 11(6/7) :687–690 (1996).

Brennen, "Sequencing by Hybridization: Methods to Generate Large Arrays of Oligonucleotides", Human Genome Program, U.S. Department of Energy, Contractor–Grantee Workshop III, (Feb. 7–10, 1993), p. 92.

Chen et al., "Synthesis of oligodeoxyribonucleotide N3'→P5' phosphoramidates" *Nucleic Acids Research* 23(14):2661–1668 (1995).

Dahl et al., "Mechanics studies on the phosphoramidite coupling reaction in oligonucleotide synthesis," *Nucleic Acids Research* 15(4):1729–1743 (1987).

Derwent Publications Ltd., London, GB; Section Ch. Week 9717, Abstract XP002101310 and JP 09 048938 (Fuji Photo Film Co. Ltd.), Feb. 1997.

Froehler et al., "Synthesis of DNA via deoxynucleoside H–phosphonate intermediates" *Nucleic Acids Res.* 14(13):5399–5407 (1986).

Gait, "Solid–phase Synthesis of Oligodeoxyribo–nucleotides by the Phosphotriester Method," *Oligonucleotide Synthesis*, M.J. Gait, ed., Oxford IRL Press, pp. 83–111 (1984).

Geysen et al., "Strategies for Epitope Analysis Using Peptide Synthesis," *J. Immunol. Meth.* 102:259–274 (1987).

Goodchild, "Conjugates of Oligonucleotides and Modified Oligonucleotides: A Review of their Synthesis and Properties," *Bioconjugate Chemistry* 1(3):165–187 (1990).

(List continued on next page.)

*Primary Examiner*—Ethan C. Whisenant
(74) *Attorney, Agent, or Firm*—Campbell & Flores LLP

(57) ABSTRACT

The present invention provides a method of biopolymer, esp. oligonucleotide, synthesis. The method consists of coupling a first nucleotide to a second nucleotide in a high surface tension solvent. The invention also provides microdroplets of a soln. comprising a solvent having a b.p. of 150 degree. C. or above, a surface tension of 30 dynes/cm or above, and a viscosity of 0.015 g/(cm)(sec), e.g., propylene carbonate. Such microdroplets are useful for the synthesis of chem. species, particularly biopolymers such as oligonucleotides and peptides, as well as arrays of chem. species. An automated system for oligonucleotide synthesis is described, which comprises delivery of microdroplets by inkjet technol. and computer control of the process. The high surface tension solvent used is selected for compatibility with the inkjet technol.

28 Claims, 18 Drawing Sheets

U.S. PATENT DOCUMENTS

| | | |
|---|---|---|
| 5,157,032 A | 10/1992 | Barton |
| 5,200,051 A | 4/1993 | Cozzette et al. |
| 5,211,747 A * | 5/1993 | Breton et al. |
| 5,212,050 A | 5/1993 | Mier et al. |
| 5,252,743 A | 10/1993 | Barrett et al. |
| 5,318,679 A | 6/1994 | Nishioka |
| 5,378,638 A | 1/1995 | Deeg et al. |
| 5,436,327 A | 7/1995 | Southern |
| 5,449,754 A | 9/1995 | Nishioka |
| 5,474,796 A | 12/1995 | Brennen |
| 5,552,270 A | 9/1996 | Khrapko et al. |
| 5,658,802 A | 8/1997 | Hayes et al. |
| 5,700,637 A | 12/1997 | Southern |
| 5,733,509 A | 3/1998 | Ackley et al. |
| 5,763,170 A | 6/1998 | Raybuck |
| 5,792,380 A * | 8/1998 | Wen et al. |
| 5,853,861 A * | 12/1998 | Held |
| 5,958,342 A * | 9/1999 | Gamble et al. |
| 5,981,733 A | 11/1999 | Gamble et al. |
| 6,028,189 A * | 2/2000 | Blanchard |

FOREIGN PATENT DOCUMENTS

| | | |
|---|---|---|
| WO | WO 95/35505 | 12/1995 |
| WO | WO 97/19749 | 6/1997 |
| WO | WO 97/44134 | 11/1997 |
| WO | WO 98/10858 | 3/1998 |
| WO | WO 98/25944 | 6/1998 |

OTHER PUBLICATIONS

Habus et al., "Improvement in the Synthesis of Oligonucleotides of Extended Length by Modification of Detritylation step," Nucleic Acids Research 22(20):4350–4351 (1994).

Kaumaya et al., "Synthesis and Biophysical Characterization of Engineered Topographic Immunogenic Determinants with αα Topology," Biochem. 29:13–23 (1990).

Khrapko et al., "An oligonucleotide hybridization approach to DNA sequencing," FEBS Letters 256(1,2):118–122 (1989).

Kirk–Othmer, "Silver to Sulfolanes and Sulfones," Encyclopedia of Chemical Technology, 3rd Edition, 21:378–391.

Kleinfeld, D., "Controlled Outgrowth of Dissociated Neurons on Patterned Substrates" J. Neurosci. 8(11):4098–4120 (1988).

Kyser et al., "Design of an impulse ink jet," J. Appl. Photographic Eng. 7:73–79 (1981).

Lam et al., "A New Type of Synthetic Peptide Library for Identifying Ligand–Binding Activity," Nature 354:82–84 (1991).

Lemmo et al., "Characterization of an Inkjet Chemical Microdispenser or Combinatorial Library Synthesis," Anal. Chem., 69:543–551 (1997).

L'opez et al., "Imaging of features on surfaces by condensation figures," Science 260 (5108):647–649 (1993).

Maskos and Southern, "A Novel method for the analysis of multiple sequence variants by hybridisation to oligonucleotides," Nucleic Acids Res. 21(9):2267–2268 (1993).

Maskos & Southern, "Oligonucleotide hybridisations on glass supports: A novel linker for oligonucleotide synthesis and hybridisation properties of oligonucleotides synthesized in situ," Nucleic Acids Res. 20(7):1679–1684 (1992).

McBride and Caruthers, "An investigation of several deoxynucleoside phosphoramidites useful for synthesizing deoxyoligonucleotides," Tetrahedron Lett 24:245–248 (1983).

Miller, "A Brief Guide to Nucleic Acid Chemistry," Bioconjugate Chemistry 1(3): 187–191 (1990).

O'Donnell–Maloney and Little, "Microfabrication and array technologies for DNA sequencing and diagnostics," Genetic Analysis: Biomolecular Engineering, 13:151–157 (1996).

Pease et al., "Light–generated oligonucleotide arrays for rapid DNA sequence analysis" Proc. Natl. Acad. Sci. USA 91(11):5022–5026 (1994).

Ramalho et al., "Introduction to Solid–Phase Oligonucleotide Chemistry," Interactiva Virtuelles Labor, http://www.interactiva.de/oligoman/intro inh.html.

Southern et al., "Analyzing and comparing nucleic acid sequences by hybridization to arrays of oligonucleotides: evaluation using experimental models" Genomics 13(4):1008–1017 (1992).

Southern et al., "Arrays of complementary oligonucleotides for analysing the hybridisation behaviour of nucleic acids," Nucleic Acids Res. 22(8):1368–1373 (1994).

Takahashi et al., "Full color ink–jet printer" NEC Res. And Develop. 80:38–41 (1986).

Weiler et al., "Combining the Preparation of Oligonucleotide Arrays and Synthesis of High–Quality Primers," Anal. Biochem. 243:218–227 (1996).

Xu et al., "Use of 1,2,4–dithiazolidine–3,5–dione (DtsNH) and 3–ethoxy–1,2,4–dithiazoline–5–one (EDITH) for synthesis of phosphorothioate–containing oligodeoxyribonucleotides," Nucleic Acids Research 24(9):1602–1607 (1996).

* cited by examiner

SOLVENT FOR BIOPOLYMER SYNTHESIS, SOLVENT MICRODROPLETS AND METHODS OF USE

This application is the National Stage of International Application No. PCT/US98/05483, filed Mar. 20, 1998, which published in English as International Publication No. WO 98/41531 and which is (i) a continuation-in-part of U.S. application Ser. No. 08/821,156, filed Mar. 20, 1997, now U.S. Pat. No. 6,028,189, and (ii) a continuation-in-part of U.S. application Ser. No. 09/008,120, filed Jan. 16, 1998, each of which is incorporated by reference herein in its entirety.

This invention was made in part with government support under NSF Grant Number BIR 9214821. The Government has certain rights in this invention.

FIELD OF THE INVENTION

The invention relates to solvents for biopolymer synthesis and the use of such solvents for assembling an array of biopolymers on a solid support.

Genetic information generated by the Human Genome Project is allowing scientists, physicians, and others to conduct diagnostic and experimental procedures on an unprecedented scale in terms of speed, efficiency, and number of screenings performed within one procedure. In order to make full use of this new information, there is an urgent need for the ability to screen a large number of chemical compounds, particularly oligonucleotide probes, against samples of DNA or RNA from normal or diseased cells and tissue. One important tool for such analyses is nucleic acid hybridization, which relies on the difference in interaction energies between complementary and mismatched nucleic acid strands (see U.S. Pat. No. 5,552,270 to Khrapko et al.). Using this tool, it is possible to determine whether two short pieces of nucleic acid are exactly complementary. Longer nucleic acids can also be compared for similarity.

Nucleic acid hybridization is often used for screening cloned libraries to identify similar, and thus presumably related, clones. This procedure typically involves using natural nucleic acid targets which are usually bound to a membrane, and a natural or synthetic nucleic acid probe which is washed over many targets at once. With the appropriate mechanics, membranes can be constructed with targets at a density of generally between one and ten targets per $mm^2$. Hybridization detection is carried out by labeling the probe, for example either radioactively or with chemiluminescent reagents, and then recording the probe's emissions onto film.

Alternative approaches to nucleic acid hybridization have involved oligonucleotide probes that are synthesized on a solid support or a substrate, and then hybridized to a single natural target. While such alternative approaches have the potential for large-scale assembly of oligonucleotide arrays, the cost of making such a variety of arrays is prohibitive.

Recently, there have been reports of using microdrop dispensers to generate oligomers and polymers arranged, on a substrate, in arrays of microdroplets:

For example, T. Brennan, Human Genome Program, U.S. Department of Energy, Contractor-Grantee Workshop III, Feb. 7–10, 1993, Santa Fe, N.M., *Methods to Generate Large Arrays of Oligonucleotides* 92 (1993), describes that arrays of oligonucleotides were sought to be synthesized in parallel chemical reactions on glass plates, using arrays of piezoelectric pumps, similar to an inkjet printer, as a means for delivering reagents. In such a scheme, each array element is separated by its neighbor by a perfluoroalkane tension barrier which is not wet by the acetonitrile reaction solvent.

U.S. Pat. No. 5,449,754 to Nishioka describes that peptide arrays can be obtained using an inkjet print head to deposit a dimethylformamide solution of N-protected activated amino acids, in the form of microdroplets, onto an aminosilylated glass slide which is subsequently washed with a trifluoroacetic acid solution to remove the N-protecting groups from the anchored amino acids. The process is repeated until amino acids having the desired sequence are obtained.

U.S. Pat. No. 5,474,796 to Brennan describes a piezoelectric impulse jet pump apparatus for synthesizing arrays of oligomers or polymers having subunits connected by ester or amide bonds. According to that scheme, a glass plate is coated with a fluoropolymer which is then selectively removed, leaving glass regions, in spots upon which oligomer or polymer synthesis would take place. The glass regions are epoxidized and subsequently hydrolyzed to afford a hydroxyalkyl group that would react with an activated chemical species. Where the oligomers sought to be synthesized are oligonucleotides, microdroplets of acetonitrile or diethyleneglycol dimethyl ether solutions of 5'-protected nucleotide monomers that are activated at their 3'-positions would be dispensed via a piezoelectric jet head, and would impinge upon the hydroxyalkyl group, forming a covalent bond therewith. After removing the 5'-protecting groups by flooding the surface of the plate with a deprotecting reagent, the process is repeated until the desired oligonucleotides are obtained.

International Publication No. WO 95/25116 by Baldeschwieler et al. describes a method for chemical synthesis at different sites on a substrate using an inkjet printing device to deliver reagents to specific sites of the substrate. The inkjet printing device is envisioned to deposit,.in repeatable sequence, (a) a protected molecule onto the substrate, (b) a deprotecting reagent onto the protected molecule so as to expose a reactive site, and (c) a second protected molecule at the site of the now-deprotected molecule, so as to form a growing chain of molecules. According to this publication by Baldeschwieler et al., useful reaction solvents are dibromomethane, nitromethane, acetonitrile and dimethylformamide.

U.S. Pat. No. 5,658,802 to Hayes et al. describes a dispensing apparatus that is allegedly capable of providing droplets having a volume of 10 pL to 100 pL, and purportedly useful for synthesizing arrays of diagnostic probes. According to that reference, the dispensing apparatus is capable of dispensing "liquids" that may contain DNA molecules, peptides, antibodies, antigens, enzymes or entire cells; however, no specific examples of such "liquids" are disclosed.

The dispensation of certain organic solvents from an inkjet printing device for use in chemical synthesis has several drawbacks. First, many organic solvents, such as alcohols or amines, bear functional groups that are capable of reacting with those chemical compounds sought to be dispensed from the inkjet device. Second, solvents having low boiling points are relatively volatile, and can evaporate from a substrate before the reactant(s) dissolved therein have completely reacted with any species bound to the substrate. Third, such volatile solvents can begin to evaporate at the site of the inkjet print head, causing reactants dissolved in the solvents to precipitate and clog the inkjet nozzle. Fourth, solvents that have low surface tension values have a relatively high affinity for the face of the inkjet nozzle, and tend to give rise to unstable and non-uniformly sized droplets. Fifth, solvents that have low viscosity values tend to form non-uniformly sized droplets due to their response to residual oscillations in the solvent. Sixth, many organic solvents, particularly acetonitrile, have the highly undesirable characteristic of being capable of dissolving adhesives and plastics used in inkjet print heads. Thus, prior to the present invention the organic solvents used for synthesizing oligonucleotides were ineffective in automated systems employing plastic components such as ink jet print heads.

The use of inkjet printing technology in chemical synthesis would be particularly useful for synthesis of a large number of different biopolymer species, such as oliognucleotides. Using a manual approach to synthesize each species would be prohibitively time consuming.

Thus, there exists a need for a method of synthesizing an array of oligonucleotides on a solid support that can be automated. In particular, there exists a need for a class of organic solvents, useful for chemical synthesis, that is relatively inert, and that has boiling point, surface tension and viscosity properties that are optimal for microdroplet formation from an inkjet device. The present invention satisfies such needs and provides related advantages as well.

Citation of any references above shall not be construed as an admission that such reference is available as prior art to the present application.

SUMMARY OF THE INVENTION

The invention provides a method of oligonucleotide synthesis. The method consists of chemically coupling a first nucleotide to a second nucleotide in a high surface tension solvent. Synthesis can be performed either through the coupling of the 5' position of the first nucleotide to the 3' position of the second nucleotide or vice versa. The high surface tension solvent can be, for example, propylene carbonate and can be used in a variety of nucleotide coupling reactions including, for example, phosphodiester, phosphotriester, phosphite triester or phosphoramidite and H-phosphonate chemistries. Additionally, the high surface tension solvent can be used with deoxyribonucleotide or ribonucleotide monomers as well as with modified nucleotides or nucleotide derivatives. The high surface tension solvent can be used with iterative coupling cycles to synthesize oligonucleotides of a desired length and sequence. Also provided is a method of oligonucleotide synthesis using a high surface tension solvent wherein the synthesis is automated.

The invention also provides a microdroplet of a solution, the solution comprising a solvent having a boiling point of 150° C. or above, a surface tension of 30 dynes/cm or above, and a viscosity of 0.015 g/(cm)(sec) or above.

The invention further provides a method for dispensing microdroplets of a solution from a microdroplet dispensing device, the microdroplet dispensing device comprising (a) a manifold which contains the solution, (b) a nozzle at one end of the manifold and (c) means for applying a pressure pulse to the manifold, the means located at the other end of the manifold, comprising the step of applying a pressure pulse to the manifold, thereby dispensing the solution through the nozzle in microdroplet form, the solution comprising a high surface tension solvent.

The invention still further provides a method for chemical synthesis, comprising the step of dispensing a microdroplet of a solution comprising (i) a first chemical species and (ii) a solvent, such that the microdroplet impinges a second chemical species and forms a third chemical species therewith, the solvent having a high surface tension.

The invention also provides a fully automated solution for synthesizing oligonucleotides, particularly deoxyribonucleosides and ribonucleosides, by repeatedly cycling a substrate through steps of depositing nucleoside monomers and of treating the substrate by rinsing off unattached nucleoside monomers. A system in accordance with the invention includes an inkjet print head for spraying nucleoside monomers on a substrate, a scanning transport for moving the substrate with respect to the print head so that the monomer is deposited at specified sites, a flow cell for treating the substrate deposited with the monomer by exposing the substrate to selected fluids, a treating transport for moving the substrate between the print head and the flow cell for treatment in the flow cell, and an alignment unit for aligning the substrate so that the substrate is correctly positioned with respect to the print head each time the substrate is positioned for deposition. Computer-controlled motion stages and vacuum chucks are used to move the substrate during deposition and to move the substrate between the print head and the flow cell.

Each time the substrate is picked up by a vacuum chuck and placed over the print head, the substrate is positionally calibrated by using a camera in conjunction with marks that are placed on the substrate the first time it is handled. Translational misalignment is corrected by moving the vacuum chuck in two axes of linear motion. Rotational misalignment is corrected by physically rotating the vacuum chuck within a substrate holder.

Software, programmed apparatuses, and computer readable memory, for carrying out the methods of the invention are also provided.

The present invention may be understood more fully by reference to the following figures, detailed description and illustrative examples which are intended to exemplify non-limiting embodiments of the invention.

DETAILED DESCRIPTION OF THE INVENTION

Microdroplets

Figure 1A:
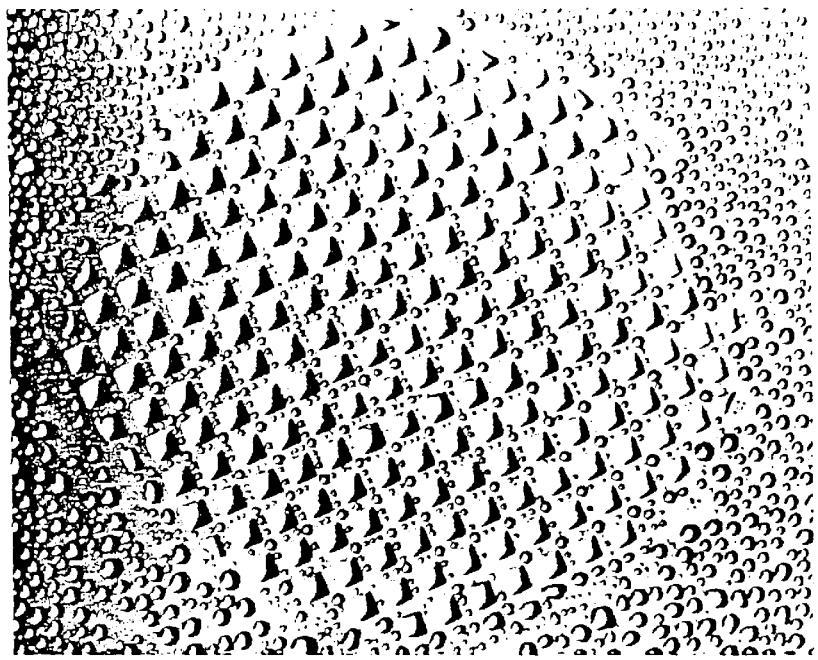
FIG. 1a is a copy of a photograph of water condensed onto an array of approximately 250 surface tension wells. Individual droplets are confined to square regions of 100 micron sides by 30 micron wide hydrophobic barriers.

The invention provides a microdroplet of a solution, the solution comprising a high surface tension solvent having a boiling point of about 150° C. or above, a surface tension of about 30 dynes/cm or above, and a viscosity of about 0.015 g/(cm)(sec) or above. Each microdroplet is a separate and discrete unit, preferably having a volume of about 100 pL or less, more preferably about 50 pL or less. Such microdroplets are useful for synthesis of chemical compounds, and in particular, for the synthesis of arrays of chemical compounds that are arranged in microdots which are separate and discrete units. It will be understood by those skilled in the art that a "solution" comprises "solvent" and "solute". In the present instance, the "solute" is preferably a chemical species that is a reagent, as described below. As used herein, "microdot" refers to a microdroplet that is associated with a substrate.

The arrays of chemical compounds synthesized by the methods of the invention are useful as libraries of chemical probes. Where the different chemical compounds obtained by the methods of the present invention are peptides, the peptide arrays can be contacted with a protein or peptide of known sequence, such as an antibody, a cell receptor or other type of receptor, so as to identify a peptide, synthesized according to the present invention, that is capable of binding to the peptide of known sequence. Such a peptide can be readily sequenced by methods well known to those skilled in the art. Where the different chemical compounds synthesized by the present invention are oligonucleotides, the oligonucleotide arrays can be used as hybridization probes, for example, for genotyping or expression analysis, e.g., as a tool in gene therapy whereby mutations may be identified in a genome, or to identify DNA in samples from the environment, or may be used to synthesize complementary oligonucleotides by using DNA polymerase and primers, or as primers for DNA sequencing or polymerase chain reaction. Where the different chemical compounds synthesized by the present invention are peptides, oligonucleotides, or other chemical species such as polysaccharides or other biologically active molecules, such chemical species can be subjected to a variety of drug screening assays to identify and ascertain their efficacy.

As stated above, the microdroplets of the present invention are in the form of separate and discrete units. By this is meant that the microdroplets that comprise the first chemical species do not intermix prior to impinging those microdots that comprise the second chemical species. As also stated above, the arrays of compounds that are obtained in accordance with the present invention are arranged in microdots which are separate and discrete units. By this is meant that each microdroplet that impinges a second chemical species is delivered such that the resulting microdots which each comprise a third chemical species do not overlap or intermingle. It is to be pointed out, however, that the second chemical species need not be arranged in separate and discrete units prior to reaction with the first chemical species; for example, a substrate having a plurality of functional groups that are not set apart from each other in separate domains can be impinged by microdroplets at separate and discrete loci, resulting in the formation of separate and discrete microdots of a third chemical species which are separated from each other via the unreacted second chemical species.

Solvents for Microdroplets

The present inventor has found, surprisingly and unexpectedly, that high surface tension solvents give rise to microdroplets that have properties that are optimal for microdroplet formation and stability, particularly when used as a reaction solvent for the synthesis of arrays of organic compounds such as oligonucleotides and peptides.

As used herein, the term "high surface tension solvent" when used in reference to chemical coupling reactions is intended to mean a solvent which exhibits a surface tension of about 30 dynes/cm or more and supports reaction cycles involving monomer addition to the growing end of an oligopolymer. The high surface tension solvents of the invention are also compatible for use with synthetic polymers such as plastics so they can be used in automated devices for synthesis or sequencing of biopolymers. A specific example of a high surface tension solvent exhibiting these characteristics is propylene carbonate. Other beneficial properties of high surface tension solvents solvents are that they can exhibit boiling point of about 150° C. or above and have viscosities of about 0.015 g/(cm)(sec) or above. For example, the high surface tension solvent propylene carbonate exhibits a surface tension of 41.1 dynes/cm, a viscosity of 0.025 g/(cm)(sec) and a boiling point of 240° C. In comparison, a solvent such as acetonitrile, which exhibits relatively low values for the above physical characteristics has a surface tension of 29.0 dynes/cm, a viscosity of 0.00375 g/(cm)(sec) and a boiling point of 81° C., and is therefore not included within the meaning of the term "high surface tension solvent." Other specific examples of high surface tension solvents that can be suitable for chemical coupling reactions include, for example, ethylene carbonate, hexamethylphosphoric triamide (HMPA), and dimethyl sulfoxide, as well as those solvents of formula (I), described below. It is to be pointed out that the boiling point, surface tension and viscosity values of the present solvents are those obtained when measured at or around 760 mm/Hg, and at or around room temperature (approximately 22° C.).

For example it has been found that microdroplets, particularly those having a volume of about 100 pL or less, that comprise solvents that have surface tensions of 30 dynes/cm or above, or thereabout, have a relatively low affinity for the face of a nozzle used to generate microdroplets and accordingly, are more stable and uniformly sized. These properties are particularly desirable when the amount of solute, e.g., a reactive chemical species, that is to be dispensed as a microdroplet solution, should preferably be uniform from microdroplet to microdroplet, such as for example in the case of organic synthesis. In addition, microdroplets that have a relatively low affinity for the face of a nozzle can be dispensed more efficiently than those that have a relatively high affinity for the face of a nozzle.

Additionally, it has been found that the present microdroplets, which comprise solvents that have boiling points of 150° C. or above, or thereabout, overcome the disadvantages of those microdroplets that comprise lower boiling solvents by not readily evaporating upon formation or deposition. This characteristic is especially important when the microdroplets are to be used as vehicles for chemical reagents: where a reactive chemical species contained in one microdroplet seeks to react with a reactive chemical species contained in a second microdroplet that is impinged by the first, the use of relatively high boiling solvent, as in present microdroplets, ensures that the solvent does not evaporate prior to reaction between the two reactive chemical species. In addition, microdroplets that are formed from solvents that have boiling points of 150° C. or above, or thereabout, do not appreciably evaporate upon formation, which prevents (a) deposition of microdroplet solutes around or within the microdroplet generating source, and accordingly prevents clogging; and (b) unwanted precipitation of solutes onto the array surface.

It has further been found that microdroplets, particularly those having a volume of about 100 pL or less, that comprise solvents that have viscosity values of 0.015 g/(cm)(sec) or above, or thereabout, do not succumb to residual oscillations caused by the microdroplet generating device and accordingly, maintain their structural integrity, e.g., spherical shape, when dispensed. This property is particularly important when the dispensed microdroplets are to be deposited in closely packed arrays of uniformly shaped microdots that cannot overlap.

In addition, solvents that have the above boiling point, surface tension and viscosity properties do not appreciably initiate the degradation or decomposition of synthetic polymers that are commonly used in microdroplet dispensing devices, allowing them to be used in conjunction with a variety of plastic parts or components.

Furthermore, where the solvent is to be used for organic synthesis, the solvent molecules must not comprise, or must not be modified so as to comprise, reactive functional groups, such as hydroxyl, primary amino, secondary amino, sulfhydryl, carboxyl, and anhydride groups, that can easily interfere, i.e., react, with a starting material, reagent, intermediate or product chemical species.

The present inventor has found that a class of organic solvents that has above, a high surface tension of about 30 dynes/cm or above and is represented by the formula (I):

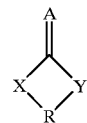

wherein
A=O or S;
X=O, S or N($C_1$–$C_4$ alkyl);
Y=O, S, N($C_1$–$C_4$ alkyl) or $CH_2$; and
R=$C_1$–$C_{20}$ straight or branched chain alkyl, is particularly preferred for use in chemical synthesis where a first chemical species is delivered to a second chemical species in the form of a microdroplet. The high surface tension solvents can additionally exhibit a boiling point of about 150° C. or above or a viscosity of about 0.015 g/(cm)(sec) or above.

As used herein, "branched chain alkyl" refers to a $C_1$–$C_{19}$ straight chain alkyl group substituted with one or more methyl, ethyl, n-propyl, isopropyl, n-butyl, isobutyl, sec-butyl, tert-butyl, n-pentyl, (1-methyl)butyl, (2-methyl)butyl, (3-methyl)butyl and neopentyl groups, or the like; wherein the total number of carbon atoms of the branched chain alkyl does not exceed twenty.

Preferably, —R— is a branched chain alkyl, and has the formula —CH($CH_3$)—, —$CH_2CH_2$—, —CH(CH($CH_3$)$_2$)—, —CH(CH($CH_3$))CH— or —$CH_2$CH($CH_3$)—. Especially preferred solvents of formula (I) include, but are not limited to:

N-methyl-2-pyrrolidone (boiling point=202° C.; surface tension=40.7 dynes/cm; and viscosity 0.017 g/(cm)(sec));

2-pyrrolidone (boiling point=245° C.; surface tension=46.9 dynes/cm; and viscosity=0.13 g/(cm)(sec));

propylene carbonate (boiling point=240° C.; surface tension=40.7 dynes/cm; and viscosity=0.025 g/(cm)(sec));

γ-valerolactone (boiling point=208° C.; surface tension=30.9 dynes/cm (at 51° C.); and viscosity=0.033 g/(cm)(sec));

6-caprolactam (boiling point=270° C.; surface tension=42 dynes/cm (at 69° C.); and viscosity=0.12 g/(cm)(sec) (at 70° C.));

ethylene carbonate (boiling point=248° C.; surface tension=42.6 dynes/cm (at 37° C.); and viscosity=0.012 g/(cm)(sec) (at 38° C.));

γ-butyrolactone (boiling point=206° C.; surface tension=36.5 dynes/cm (at 43° C.); and viscosity=0.017 g/(cm)(sec));

δ-valerolactone (boiling point=218–220° C.; surface tension and viscosity values not available);

1,3-dimethyl-3,4,5,6-tetrahydro-2(1H)-pyrimidinone (boiling point=230° C. (754 mm/Hg); surface tension=36.12 dynes/cm; and viscosity=0.029 g/(cm)(sec));

ethylene trithiocarbonate (boiling point=307° C.; surface tension and viscosity values not available); and 1,3-dimethyl-2-imidazolidinone (boiling point=220° C. (754 mm/Hg; surface tension=37.6 dynes/cm; and viscosity=0.019 g/(cm)(sec)).

Propylene carbonate solvent is most preferred.

It is to be pointed out that boiling point values increase as the pressure increases, and surface tension and viscosity values increase as the temperature decreases. Accordingly, the boiling point values are higher at 760 mm/Hg than at certain lower pressures reported above, and the surface tension and viscosity values are higher at room temperature than at certain higher temperatures reported above.

It is also to be pointed out that the solvents of the invention do not necessarily have to exhibit all three characteristics of having a boiling point of about 150° C. or above, a surface tension of about 30 dynes/cm or above, and a viscosity of about 0.015 g/(cm)(sec) or above to be useful in the methods, apparatus or automated system of the invention. For example, solvents which exhibit less than the values described above for one or more of the three physical properties can also be used so long as the solvents maintain their ability to support biopolymer synthesis. Such solvents should additionally be capable of forming discrete microdroplets without substantially initiating degradation of components of the apparatus or automated system.

Such solvents can exhibit, for example, less than the values described for one or more of three physical properties which can be compensated by an uncharacteristically high value of another one of the above physical properties, so long as the solvents support biopolymer synthesis. Moreover, solvents that have values less than those described above for either boiling point, surface tension or viscosity can similarly be compensated by, for example, substituting or modifying the components of the apparatus so as to maintain the ability of the ink jet head, for example, to dispense discrete microdroplets of solvent. Thus, the solvents of the invention can exhibit values for one or more physical properties less than those described above so long as they maintain their function of supporting biopolymer synthesis in microdroplets. Given the teachings herein, those skilled in the art will know or can determine which solvents can be used in the methods of the invention.

Preparation of Microdroplets

The microdroplets of the present invention are preferably obtained by forcing the solvent, at a rate of about 1 to about 10 m/sec, through an orifice or nozzle that has a diameter of about 10 to about 100 $\mu$m. It is critical that the microdroplets so obtained are dispensed from the orifice or nozzle in the form of separate and discrete units.

Figure 1B:
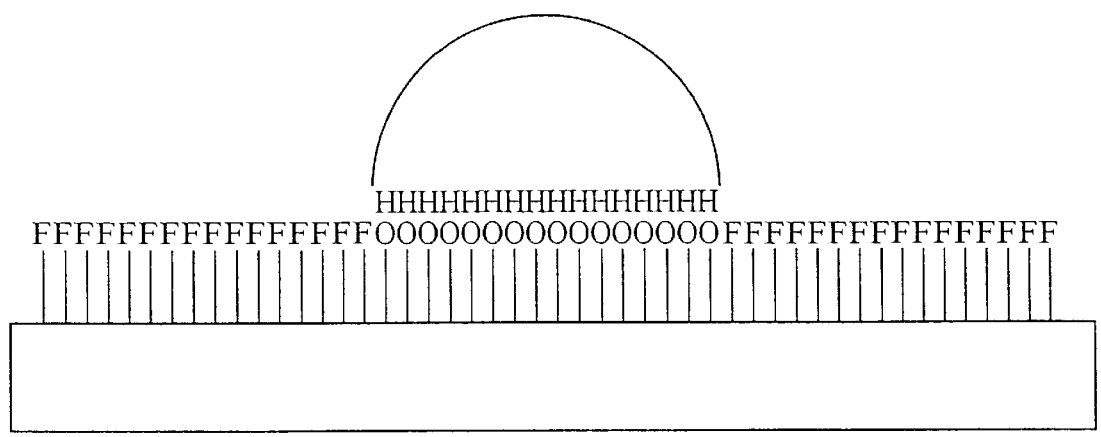
FIG. 1b is a side view of a surface tension well showing the arrangement of hydrophilic and hydrophobic regions, and a cross section of a reagent drop sitting on an hydroxylated hydrophilic surface. The bottom layer substrate is silicon dioxide, and repeating units of —F represent a perfluorinated hydrophobic surface. The reagent drop sits on repeating —OH units of the silicon dioxide support. The diameter of the reagent drop is approximately 100 $\mu$m.

One embodiment of the invention involves a system utilizing a mechanism for localizing and separating microdroplets preferably having a volume of about 100 pL or less, more preferably about 50 pL or less. The microdroplets are separated from each other, in the form of microdots by, for example, hydrophobic domains. At such small solvent volumes, surface tension is the strongest force that acts on a microdroplet, and can be used, for example, to create circular "surface tension wells" (FIG. 1$a$ and FIG. 1$b$), preferably arranged in arrays of microdots. Such surface tension wells can constrain each microdot, and prevent adjacent microdots from overlapping or merging with each other. According to the invention, methods have been developed that produce an array of microdots that are in the form of circular wells. The microdots define the locations of the array elements, and act as miniature reaction vessels for chemical synthesis. The microdots can vary in size and will depend on the intended use of the synthesized array. For example, the diameter of each microdot can be greater than 1000 $\mu$m, but typically ranges from about 1 to about 1000 $\mu$m, preferably from about 10 to about 500 $\mu$m, and more preferably from about 40 to about 100 $\mu$m. Similarly, the distance between adjacent microdots will vary according to the intended use of the array. The distance between each microdot is typically from about 1 to about 500 $\mu$m, preferably from about 10 to about 100 $\mu$m, and more preferably from about 20 to about 30 $\mu$m. Those skilled in the art will know or can determine without undue experimentation what is the appropriate separation of microdots within an array for a particular use.

Physical separation of circular wells can be accomplished according to known methods. For example, such methods can involve the creation of hydrophilic wells by first applying a protectant, or resist, over selected areas over the surface of a substrate. The unprotected areas are then coated with a hydrophobic agent to yield an unreactive surface. For example, a hydrophobic coating can be created by chemical vapor deposition of (tridecafluorotetrahydrooctyl)-triethoxysilane onto the exposed oxide surrounding the protected circles. Finally, the protectant, or resist, is removed exposing the well regions of the array for further modification and nucleoside synthesis using the high surface tension solvents described herein and procedures known in the art such as those described by Maskos & Southern, *Nucl. Acids Res.* 20:1679–1684 (1992). Alternatively, the entire surface of a glass plate substrate can be coated with hydrophobic material, such as 3-(1,1-dihydroperfluoroctyloxy) propyltriethoxysilane, which is ablated at desired loci to expose the underlying silicon dioxide glass. The substrate is then coated with glycidyloxypropyl trimethoxysilane, which reacts only with the glass, and which is subsequently "treated" with hexaethylene glycol and sulfuric acid to form an hydroxyl group-bearing linker upon which chemical species can be synthesized (U.S. Pat. No. 5,474,796 to Brennan). Arrays produced in such a manner can localize small volumes of solvent within the circular wells by virtue of surface tension effects (L'opez et al., *Science* 260:647–649 (1993)).

The protectant, or resist, can be applied in an appropriate pattern by, for example, a printing process using a rubber stamp, a silk-screening process, an inkjet printer, a laser printer with a soluble toner, evaporation or by a photolithographic process, such as that reported by Kleinfeld, D., *J. Neurosci.* 8:4098–4120 (1988). The hydrophobic coating can also be applied directly in any appropriate pattern by, for example, a printing process using a rubber stamp, a silk-screening process, or laser printer with a hydrophobic toner.

Additionally, the use of the present solvents allows for the direct synthesis of chemical compound arrays onto a substrate such as a silicon wafer or a glass slide without the need for creating hydrophilic wells. Such direct synthesis is accomplished, for example, by accurately depositing a microdroplet of a solution comprising a first chemical species, at each loci of the array. As described above, inkjet print heads can be used for accurately dispensing microdroplets in either single or multiple dispenser format, i.e., from either a single nozzle or from multiple nozzles, or with the dispensation of either a single microdroplet or of multiple microdroplets.

The present invention also encompasses a method for delivering a first chemical species to an appropriate locus of the substrate. In one embodiment, microfabricated piezoelectric pumps, or nozzles, similar to those used in inkjet printers, are used to deliver a specified volume of solution to an appropriate locus of the substrate (Kyser et al., *J. Appl. Photographic Eng.*, 7:73–79 (1981)).

Figure 2:
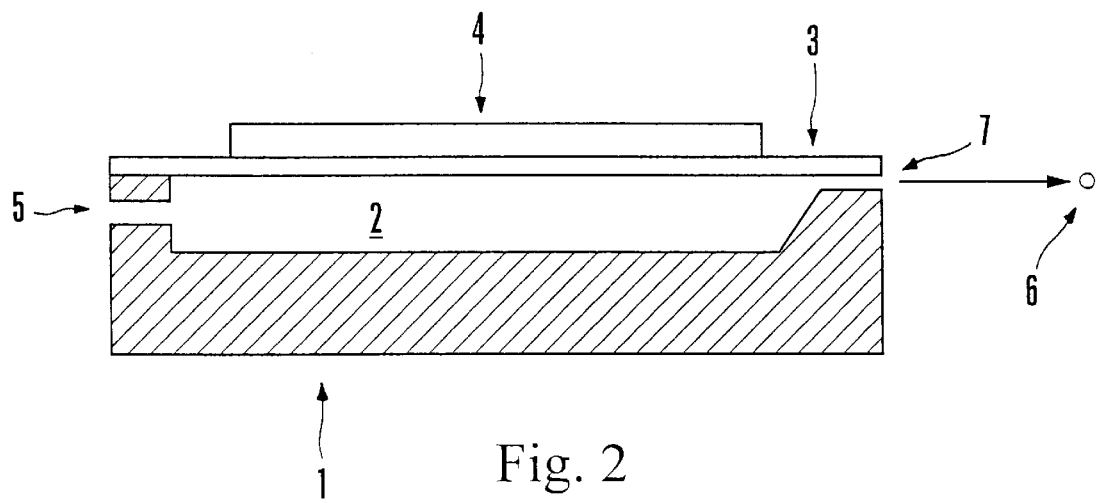
FIG. 2 is a schematic diagram of a piezoelectric pump in an inkjet print head.

FIG. 2 shows an example of a piezoelectric pump, described by way of example but not limitation as follows: The piezoelectric pump is made by using etching techniques known to those skilled in the art to fabricate a shallow cavity in silicon base 1. A thin, glass membrane 3 is then anodically bonded to silicon base 1 to seal the etched cavity, thus forming a small cavity 2 with narrow inlet 5 and nozzle 7. When the end of inlet 5 of the piezoelectric pump is dipped in the reagent solution, capillary action draws the liquid into the cavity 2 until it comes to the end of the nozzle 7. When an electrical pulse is applied to the piezoelectric element 4 glued to the glass membrane it bows inward, ejecting a microdroplet 6 out of the nozzle at the end of the piezoelectric pump. The cavity refills itself through inlet 5 by capillary action. Simple designs for piezoelectric pumps will operate at 1 thousand cycles per second (kilo Hertz or kHz), while more advanced designs operate at 6 kHz (See Takahashi et al., *NEC Res. and Develop.* 80:38–41 (1986)).

For chemical synthesis in two dimensional arrays, piezoelectric pumps that will deliver on demand microdroplets having a volume of about 100 pL of less, at rates of several hundred Hz, are preferred. However, the microdroplet volume or speed at which the piezoelectric pump can operate may vary depending on the need. For example, if an array having a greater number of microdots but with the same array surface area is to be synthesized, then smaller microdroplets should be dispensed. Additionally, if synthesis time is to be decreased, then the operation speed of the microdroplet dispensing device can be increased. Adjusting such parameters is within the purview of one skilled in the art, and can be performed according to the need.

Figure 3:
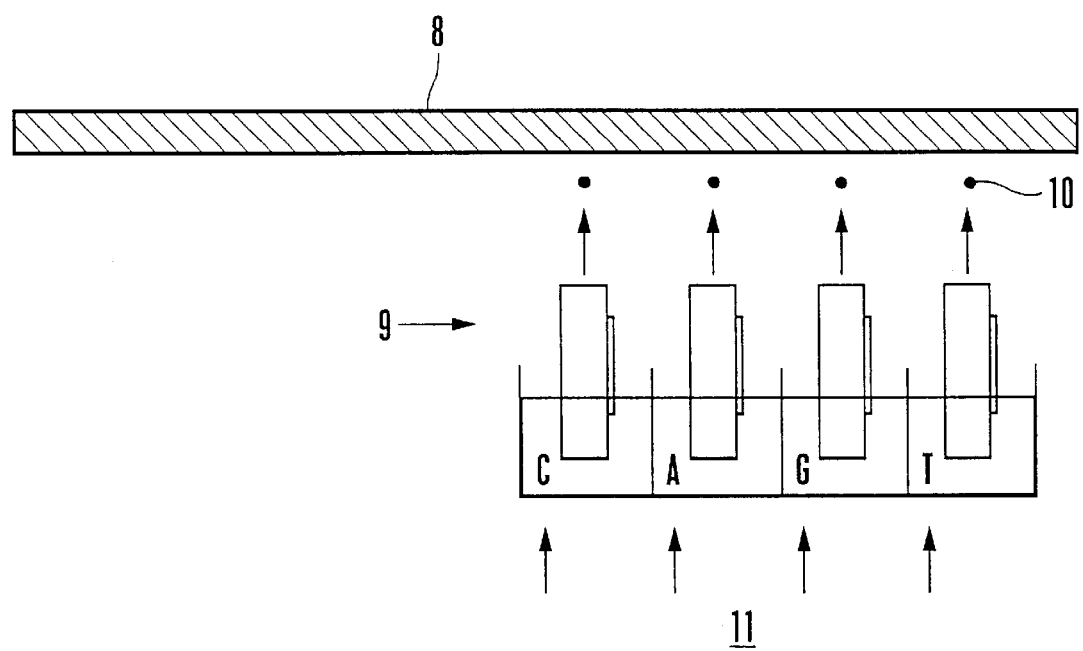
FIG. 3 shows the substrate with surface tension wells, moved by an X-Y translation stage, above the nozzles spraying microdroplets.

FIG. 3 shows substrate 8 being "scanned" (moved) across a set of nozzles 9 using a computer-controlled X-Y translation stage which translocates the nozzles relative to the substrate, or preferably, translocates the substrate relative to the nozzles. The computer synchronizes and times the firing of the nozzles 9 to deliver a single microdroplet 10 of the appropriate first chemical species 11 to each locus of the substrate.

Figure 4:
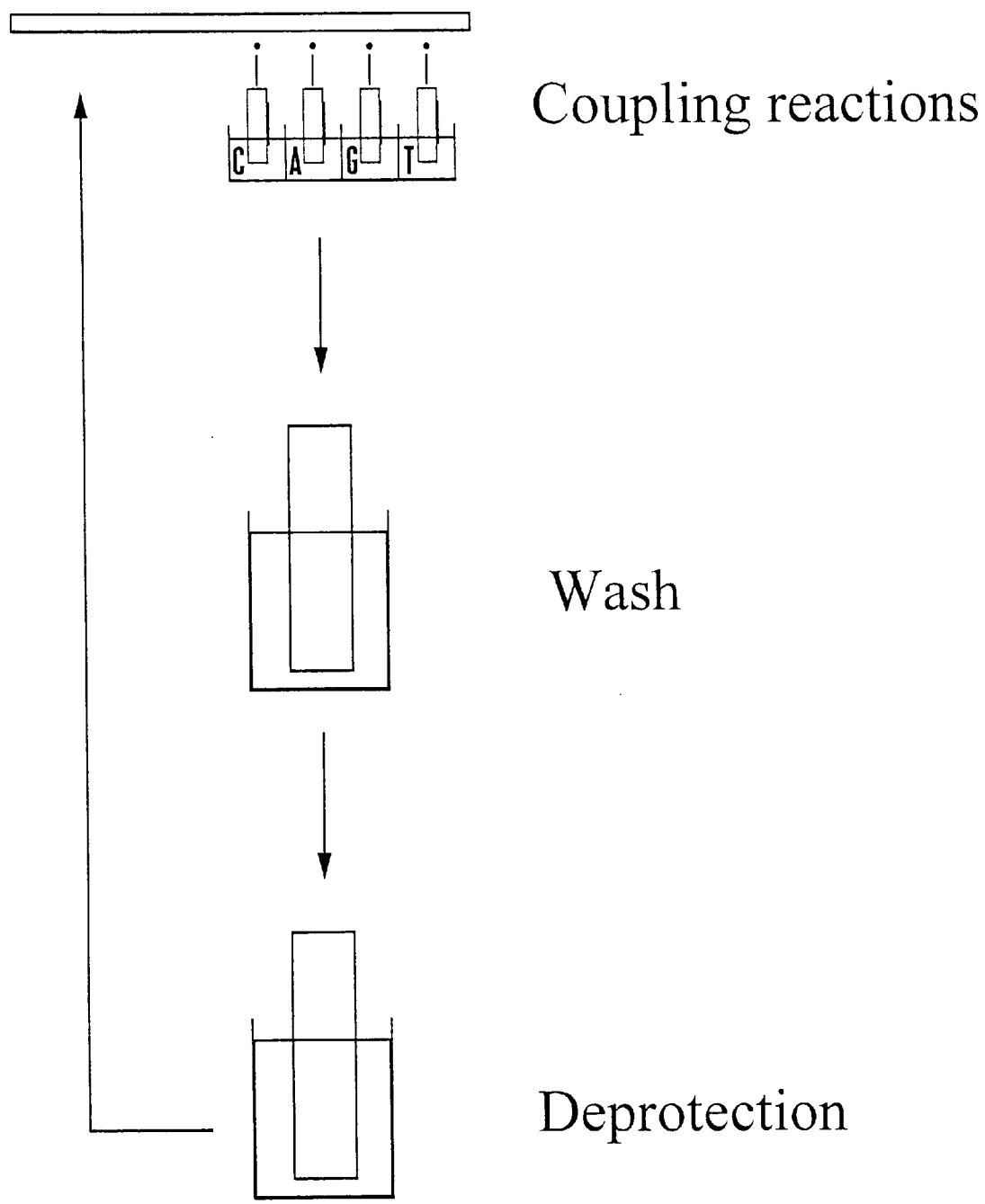
FIG. 4 is a scheme showing a complete cycle of oligonucleotide synthesis comprising (a) delivering a reactant to each well, (b) washing away unreacted monomers, and (c) deprotecting the ends of the extended molecules.

FIG. 4 illustrates a cycle to synthesize an oligonucleotide. It begins by delivering a solution comprising an appropriately functionalized nucleoside either along with a catalyst such as 5-ethylthiotetrazole premixed with the nucleoside, or separately, from a separate nozzle, to each well on the substrate. The entire substrate can then be rinsed to remove excess monomer; exposed to an oxidizing solution, typically an iodine/tetrahydrofuran/pyridine/water mixture; and then rinsed with acid to deprotect the 5' end of the oligonucleotide in preparation for the next round of synthesis. The rinses can be common to all the microdots of the substrate and can be performed, for example, by bulk immersion of the substrate. One such iteration adds a first chemical species to each growing oligomer; thus, an array of oligomers having a length of ten units each requires 10 such iterations.

The number of iterations, and therefore, the length of the oligomers obtained, will be determined by the need and desired use for the array. As such, the oligomer lengths which can be achieved using the methods of the invention are limited only by existing coupling chemistries. Routinely, oligomers having about 10 to about 100, and preferably having about 20 to about 60 units each can be synthesized. As new coupling chemistries emerge, so will the yield and length of oligomeric products. Therefore, it is envisioned that the methods of the invention are useful for the synthesis of oligomer arrays of greater than 100 units each.

Inkjet printers generally contain print heads having 50 to 100 independently controlled nozzles. With each nozzle operating at several hundred Hz, an apparatus with five such heads can deliver a microdroplet of a solvent comprising a first chemical species to 100,000 different loci in a matter of seconds. A complete synthesis cycle can take, for example, 5 minutes, or just over 2 hours for an array of 100,000 oligomers having 25 units each. Inkjet print heads having a greater or fewer number of nozzles, and which operate at different speeds, can be used as well. Additionally, multiple heads can be simultaneously used to synthesize the arrays. Such modifications are known to those skilled in the art and will vary depending on the size, format and intended use of the assay.

Chemical Synthesis Using High Surface Tension Solvents

The high surface tension solvents described above in reference to microdroplets also can be used in a variety of chemical synthesis modes and formats other than those described herein using microdroplets and automated systems. Such synthesis modes and formats include, for example, the synthesis of biopolymers such as oligonucleotides and peptides.

Therefore, the invention provides a method of oligonucleotide synthesis in a high surface tension solvent. The method consists of chemically coupling a first nucleotide with a second nucleotide or an oligonucleotide in the high surface tension solvent under conditions which allow covalent bond formation between the first and second nucleotide or between the first nucleotide and the oligonucleotide. The covalent bond formation joins the 5' position of the first nucleotide with the 3' position of the second nucleotide so as to form an oligonucleotide product of two or more nucleotide units. Alternatively, coupling can proceed in the opposite direction. As described further below in reference to oligonucleotide synthesis in microdroplets, the first or second nucleotide can be, for example, a nucleoside, activated nucleoside, modified nucleoside, nucleoside derivative, nucleotide monomer or oligonucleotide.

Nucleotide linkages other than between the 5' and 3' positions of nucleotides also exist and can be synthesized by methods known to those skilled in the art. Such methods and chemistries are described more fully below in reference to oligonucleotide synthesis in microdroplets. For example, synthesis methods exist for the covalent bond formation between the 5' positions of two nucleotides, or between the 5' position of a nucleotide and the 5' position of an oligonucleotide chain. Similarly, synthesis methods exist for the covalent bond formation between the 3' positions of two nucleotides, or between the 3' position of a nucleotide and the 3' position of an oligonucleotide chain. In addition, reagents for synthesizing all of the above linkages using a variety of chemistries are commercially available and are known to those skilled in the art.

Oligonucleotide synthesis in a high surface tension solvent can be performed, for example, using any of a variety of chemistries and methods known to those skilled in the art. The choice of which chemistry to use with the high surface tension solvents of the invention will depend on the particular application and preference of those in the field of oligonucleotide chemistry. The methods described herein employing high surface tension solvents in oligonucleotide coupling reactions can be used with known chemistries by substituting a known coupling buffer or solvent with a high surface tension solvent. These chemistries will be described more fully below in reference to oligonucleotide synthesis in microdroplets.

Assembly of oligonucleotide chains is most reproducibly accomplished using a commercial DNA synthesizer, but a manual flow system or even a small sintered glass funnel can be substituted in the methods of the invention. Additionally, the automated system described herein can also be used to synthesize diverse populations of oligonucleotides in two-dimensional arrays. Although machine specifications can vary considerably, the basic steps involved in assembly of oligonucleotides are set forth in Example II for the specific example of using phosphoramidite chemistry to synthesize two-dimensional oligonucleotide arrays using an inkjet print head.

Therefore, the invention provides a method of oligonucleotide synthesis using a high surface tension solvent wherein the synthesis is automated and is performed on a solid support. The invention also provides for methods of oligonucleotide synthesis using a high surface tension solvent wherein synthesis is automated so as to produce a two dimensional array of a plurality of different oligonucleotides on a solid support.

Synthesis of oligoribonucleotides can similarly be accomplished using the high surface tension solvents of the invention, as described below in reference to synthesis in microdroplets. The choice of which chemistry to use with the high surface tension solvents of the invention will depend on the particular application and preference of those in the field of oligoribonucleotide chemistry.

The high surface tension solvents of the invention can also be used in synthesis of peptides. For example, a reaction between a first amino acid and a second amino acid in the presence of a catalyst can take place in a high surface tension solvent. Chemistries for peptide synthesis in a high surface tension solvent are similarly described more fully below in reference to peptide synthesis in microdroplets.

Chemical Synthesis Using Microdroplets

The microdroplets of the present invention further comprise a first chemical species which is soluble in a high surface tension solvent of the invention. Typically, upon formation, the microdroplet is a solution of the first chemical species having a concentration of about 1 nM to about 5M, preferably from about 0.01 mM to about 1M. The microdroplet impinges a second chemical species, and the first chemical species of the microdroplet reacts with the second chemical species to form a third chemical species, the third chemical species being different from the first and second chemical species. In this manner, and particularly when the second chemical species is linked to a substrate, arrays of different chemical compounds, arranged in microdots which are separate and discrete units, can be synthesized.

The first chemical species is any chemical compound that can react with a second chemical species so as to form a third chemical species. The first chemical species and the second chemical species can be the same or different, but the third chemical species must be different from the first chemical species and the second chemical species. The process of reacting a first chemical species with a second chemical species to form a third chemical species may be repeated at the site of the third chemical species, such that in a subsequent iteration of the process, the third chemical species becomes the "second chemical species" with respect to an impinging microdroplet comprising a first chemical species, and the reaction product of that "second chemical species" and the first chemical species is a new third chemical species that is different from the original third chemical species. Accordingly, as used herein, "second chemical species" is that which reacts with a first chemical species, and "third chemical species" is the reaction product of the first chemical species and second chemical species. An unlimited number of iterations of this process can be performed until the desired chemical compound is synthesized. In a specific embodiment, the third chemical species is an oligomer (e.g., a homo-oligomer or hetero-oligomer), preferably a biopolymer, containing as monomer units the first and second chemical species.

In one embodiment, the first chemical species reacts with the second chemical species in the presence of a catalyst. Accordingly, the solution can optionally comprise a catalyst, such as an enzyme or other chemical catalyst, that accelerates the rate of reaction between the first chemical species and second chemical species. Alternatively, if it is advantageous that the first chemical species react with the second chemical species in the presence of a catalyst, a solution comprising a catalyst can be delivered to the locus where the first chemical species impinges the second chemical species either prior or subsequent to the impingement of the second chemical species by the first chemical species.

For ease of handling, the second chemical species can be associated with a substrate. By "associated with" is meant (a) adheres, but is not chemically attached to, such as for example where the second chemical species is in the form of a microdot on a substrate of paper or untreated glass, or in solution sitting in a microwell or microcavity of the substrate; or (b) is chemically attached to, such as for example where the second chemical species is covalently bonded directly to a functional group of the substrate, or bonded to a linker that is attached to the substrate.

As used herein, the term "substrate" is intended to mean a generally flat surface, porous or not, which has, or can be chemically modified to have, reactive groups suitable for attaching further organic molecules. Examples of such substrates include, but are not limited to, glass, silica, silicon, polypropylene, TEFLON®, polyethylimine, nylon, fiberglass, paper, and polystyrene. Bead structures may also be attached to the surface of the substrate, wherein the beads are composed of one or more of the preceding substrate materials. As used herein, substrates which contain or are modified to contain chemically reactive species can therefore also be referred to as a "chemical species."

Where the third chemical species is to be assayed, for example, for biological activity, it is preferable that the third chemical species be readily removable from the substrate: e.g., in the case where the third chemical species adheres, but is not chemically attached, to, the substrate, by washing with a suitable solvent; in the case where the third chemical species is in solution sitting in a microwell or microcavity of the substrate, by removing the solution via a micropipetting or microsyringing device; and in the case where the third chemical species is chemically attached to the substrate (either directly or via a linker), by releasing, preferably hydrolyzing or enzymatically cleaving, the third chemical species from the substrate or linker attached to the substrate. It will be understood that in the latter instance, the third chemical species so released will be slightly chemically modified relative to the attached third chemical species; for example, where the third chemical species is attached to an hydroxyl or amino group of the substrate via an ester or amide bond, the third chemical species so hydrolyzed will have a terminal carboxyl or carboxylate group. Accordingly, the term "third chemical species" is also meant to encompass the chemical species that is ultimately released from the substrate.

In one embodiment, the first chemical species is, for example, a nucleoside, activated nucleoside, or nucleotide; the second chemical species is, for example, a substrate having reactive functional groups, a linker attached to a substrate, or a nucleoside, nucleotide, or oligonucleotide attached to either the linker or directly to the substrate; and the third chemical species is a nucleoside, activated nucleoside, or nucleotide (in the case where the second chemical species is a substrate or linker attached to a substrate) or an oligonucleotide of at least two nucleoside units (in the case where the second chemical species is a nucleoside or oligonucleotide), chemically attached to either the linker or directly to the substrate.

Preferably, the first chemical species is a nucleoside having an activated phosphorous-containing, preferably a phosphoramidite, group at the 3' position, and a protected hydroxyl group at the 5' position, and the second chemical species is (a) a substrate or linker attached to a substrate having an thiol or hydroxyl group that is capable of forming a stable, covalent bond with the phosphoramidite group at the 3' position of the first chemical species, or (b) a nucleoside or oligonucleotide attached to either the linker or directly to the substrate, and having an thiol or hydroxyl group at its 5' position that is capable of forming a stable, covalent bond with the phosphoramidite group at the 3' position of the first chemical species.

Thus, where the first chemical species is a nucleoside, the present invention encompasses a solution, preferably in microdroplet form, comprising a high surface tension solvent and a nucleoside. The solvent may additionally have a high boiling point or a high viscosity. Preferably, the solvent is represented by the formula (I), described above.

As used herein, the term "nucleoside" encompasses both deoxyribonucleosides and ribonucleosides, and the term "oligonucleotide" refers to an oligonucleotide that comprises deoxyribonucleotide or ribonucleotide units, such that the term "oligonucleotide" encompasses both oligodeoxyribonucleotides and oligoribonucleotides.

Where the first chemical species and second chemical species bear additional reactive groups, such as for example primary amino groups of adenine, cytosine and guanine bases, those reactive groups can have additional protecting groups, so as to preclude unwanted side reactions if not protected. The primary amino groups of adenine, cytosine and guanine bases are protected with amino protecting groups well known to those skilled in the art, preferably, with t-butylphenoxyacetyl (tBPA) groups.

Typically, by way of example, a solution comprising a nucleoside as the first chemical species and having (a) a protecting group, preferably a monomethoxytrityl or dimethoxytrityl protecting group, on the 5' hydroxyl group, (b) an activated phosphorous-containing group at the 3' position, and (c) another protecting group, preferably a tBPA group, at any primary amino group of the base portion of the nucleoside, in a solvent of the invention is dispensed as a microdroplet onto a second chemical species, e.g., a substrate or a substrate with a linker having, for example, hydroxyl functional groups.

Suitable nucleosides useful for the synthesis of oligonucleotides according to the present methods are those nucleosides that contain activated phosphorous-containing groups such as phosphodiester, phosphotriester, phosphate triester, H-phosphonate and phosphoramidite groups. It will be understood that where the first chemical species is a nucleoside, and the second chemical species is a nucleoside or an oligonucleotide, the first and second chemical species have the same activated phosphorous-containing group. Such activated nucleosides and their relevant chemistries are described in, for example, *Nucleic Acids in Chemistry and Biology* (Blackburn and Gait eds., 2d ed. 1996) and T. Atkinson et al., *Solid-Phase Synthesis of Oligodeoxyribonucleotides by the Phosphite-Triester Method*, in *Oligonucleotide Synthesis* 35–39 (M. J. Gait ed., 1984). Preferably, the activated phosphorous-containing group is a phosphoramidite, more preferably a phosphoramidite having a cyanoethyl group, and most preferably, a phosphoramidite having the formula $(iPr_2N)P(OCH_2CH_2CN)OR$, where R is the 3' position of a nucleoside. By way of example but not limitation, a detailed example of oligonucleotide synthesis using a phosphoramidite nucleoside derivative is described below.

The reaction between the 3' phosphoramidite group of the nucleoside, and the hydroxyl groups of the substrate-bound linker, is facilitated by a catalyst, such as 5-methylthiotetrazole, tetrazole, or preferably 5-ethylthiotetrazole. The solution of nucleoside can additionally comprise the catalyst or preferably, following dispensation of the nucleoside solution, an additional microdroplet of catalyst solution can be dispensed upon the locus at which the nucleoside solution impinged the substrate-bound linker. The reaction between the hydroxyl groups of the substrate-bound linker, and the 3' phosphoramidite group of the nucleoside, preferably performed in the presence of the catalyst, forms a protected nucleoside anchored to the substrate via a 3' phosphite group. This protected nucleoside is now the third chemical species. Preferably, the entire substrate is washed with a solvent, e.g., acetonitrile or dichloromethane, before proceeding to the next step. It will be appreciated that a phosphoramidite group will form a phosphite group, preferably in the presence of a catalyst, with a hydroxyl group in general. Such an hydroxyl group may be either a primary, secondary or tertiary alcohol, or may be of a silanol. The phosphite group is oxidized to a phosphate group in the presence of an oxidizing agent. Additionally, a phosphoramidite group will form a thiophosphite group, preferably in the presence of a catalyst, with a thiol group in general. Such a thiol group may be either a primary, secondary or tertiary thiol. The thiophosphite group can be oxidized to a thiophosphate group in the presence of an oxidizing agent.

The resulting 3' phosphite group is then oxidized to a 3' phosphate group. Preferably, the oxidizing agent used to oxidize the phosphite group to the phosphate group is iodine, more preferably, a solution of iodine, water, an organic base such as pyridine, and an organic solvent such as tetrahydrofuran. Preferably, the entire substrate, to which the nucleoside having the 3' phosphite group is attached, is washed with the oxidizing agent, oxidizing the 3' phosphate group to the 3' phosphate group. In one embodiment of the invention, the substrate, to which the nucleoside having the 3' phosphite group is attached, is submerged in a bath containing the oxidizing agent. Alternatively, the oxidizing agent can be dispensed as a microdroplet onto the locus at which the nucleoside, having the 3' phosphite group, is synthesized. In such an instance, the oxidizing agent is preferably dispensed as a solution in a high surface tension solvent. Following treatment with the oxidizing agent, and before proceeding to the next step, the entire substrate is preferably washed with a solvent, e.g., acetonitrile or dichloromethane.

Following oxidation, the entire substrate, to which the nucleoside having the 3' phosphate group is attached, is treated with a reagent that "caps" the unreacted hydroxyl groups of the substrate-bound linker so as to prevent them from competing for the phosphoramidite group of a subsequently dispensed nucleoside with the 5' position of the newly added nucleoside, above. Preferably, the capping reagent is an acylating agent, more preferably, an acyl halide and most preferably, perfluorooctanoyl chloride. Preferably, the entire substrate is washed with a solvent, e.g., acetonitrile or dichloromethane, before proceeding to the next step.

In the next step, the nucleoside having the 3' phosphate group that is covalently bonded to the linker of the substrate is treated with a first deprotecting agent which removes the protecting group from the bound nucleoside's 5' position, exposing a reactive hydroxyl group at the 5' position. Preferably, the first deprotecting agent is an acid, and more preferably dichloroacetic acid. In a preferred embodiment, the entire substrate to which the nucleoside having the 3' phosphate group is bonded is rinsed with a solution of the first deprotecting agent. Alternatively, the first deprotecting agent can be dispensed as a microdroplet; in such a case, the microdroplet preferably comprises a high surface tension solvent. Before proceeding to the next step, the entire substrate is preferably washed with a solvent, e.g., acetonitrile or dichloromethane.

In the following step, a second nucleoside having an activated phosphorous-containing, preferably a phosphoramidite, group at the 3' position, and a protected hydroxyl group at the 5' position, is dispensed as a microdroplet solution using a high surface tension solvent so as to impinge the microdot.

The solution of nucleoside can additionally comprise a catalyst, or alternatively, in a subsequent step, a microdroplet of a solution of catalyst, such as 5-methylthiotetrazole, tetrazole, or preferably 5-ethylthiotetrazole, preferably in a high surface tension solvent, is dispensed upon the locus at which the second nucleoside solution impinged the microdot. The catalyst facilitates a reaction between the 5' hydroxyl group of the first nucleoside and the 3' phosphoramidite group of the second nucleoside, resulting in the coupling of the second nucleoside to the first nucleoside via a phosphite group, as described above.

At this point, successive iterations of (a) oxidizing the resulting phosphite to a phosphate group; (b) removing the 5' protecting group; (c) dispensing an additional protected nucleoside having a phosphoramidite group at its 5' position, optionally in the presence of catalyst or, preferably; (d) dispensing the catalyst at the locus where the additional nucleoside was dispensed, preferably with solvent washing subsequent to performing each of iterative steps (a)–(d), affords a linker-bound oligonucleotide that has a 2-cyanoethylphosphate group, as well as a protecting group, preferably a tBPA protecting group, on any primary amino group of the nucleoside bases.

Treatment with a second deprotecting agent, preferably ethanolamine, removes the protecting groups from the nucleoside bases, and converts the oligonucleotide 2-cyanoethylphosphate groups to phosphate groups. Preferably, the entire substrate to which the oligonucleotide is bonded is rinsed with a solution of the second deprotecting agent. Alternatively, the second deprotecting agent can be dispensed as a microdroplet; in such a case, the microdroplet preferably comprises a high surface tension solvent.

The chemistry relating to the above-described example of oligonucleotide synthesis is summarized below in Scheme 1:

SCHEME 1

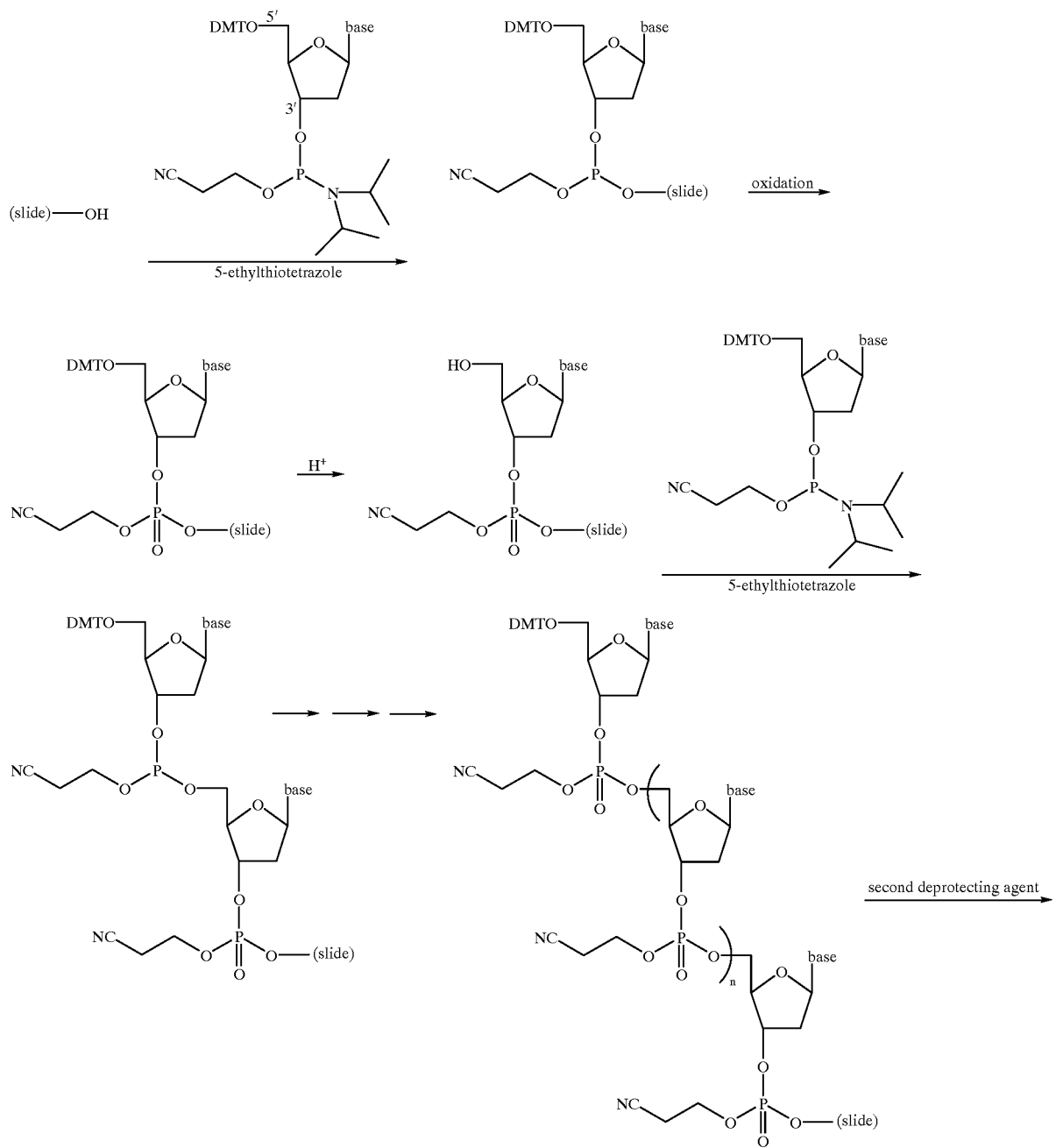

-continued

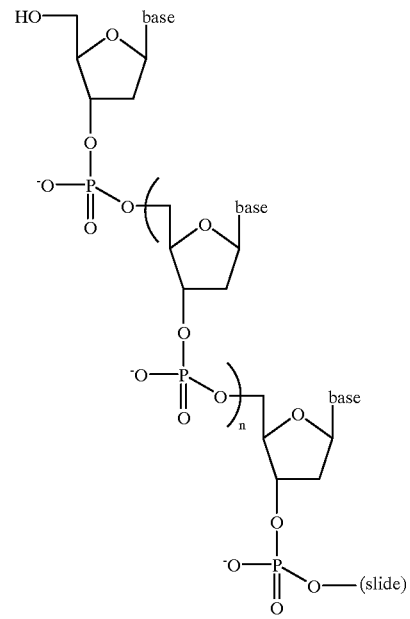

It is to be pointed out that this process may be repeated at different loci of the substrate, using different first chemical species and second chemical species, so as to obtain, if desired, a different oligonucleotide at each loci.

The oligonucleotides thus synthesized can be used in their substrate-anchored form, e.g., in hybridization assays conducted on the substrate. Alternatively, in another embodiment of the invention, the substrate-anchored oligonucleotides obtained above can be cleaved from the substrate. In a specific embodiment, the nucleoside unit of the oligonucleotide that is directly attached to the substrate, or, attached to a linker that is attached to the substrate, is attached to the substrate, or to the linker, via an ester bond. Such an ester bond is susceptible to hydrolysis via exposure to a hydrolyzing agent. Such an ester bond is preferably formed on the first nucleoside prior to application to the substrate. In this embodiment, prior to synthesis of the oligonucleotide to be cleaved, an amino group, preferably in the form of a long chain alkylamine, is attached to the substrate (see T. Atkinson et al., Solid Phase Synthesis of Oligodeoxyribonucleotides by the Phosphitetriester Method, in Oligonucleotide Synthesis (M. J. Gait ed., 1984). The first nucleoside having the ester bond is attached to the amino group of the substrate via an activated O-succinate group (Scheme 2, below, and T. Atkinson et al., Solid-Phase Synthesis of Oligodeoxyribonucleotides by the Phosphitetriester Method, in Oligonucleotide Synthesis (M. J. Gait ed., 1984), which reacts with the amino group of the substrate to form an amide bond therewith. As used herein, "activated" O-succinate groups are those that have, at the succinate carbonyl group not attached to the nucleoside, a leaving group that is capable of being displaced by an amino group, preferably an amino group of a substrate. Preferably, the activated O-succinate group is one that has, at the succinate carbonyl group not attached to the nucleoside, a p-nitrophenoxy group. Methods for preparing activated O-succinate groups are well known to those skilled in the art. Such an activated nucleoside can be applied to the substrate as a microdroplet solution.

Scheme 2

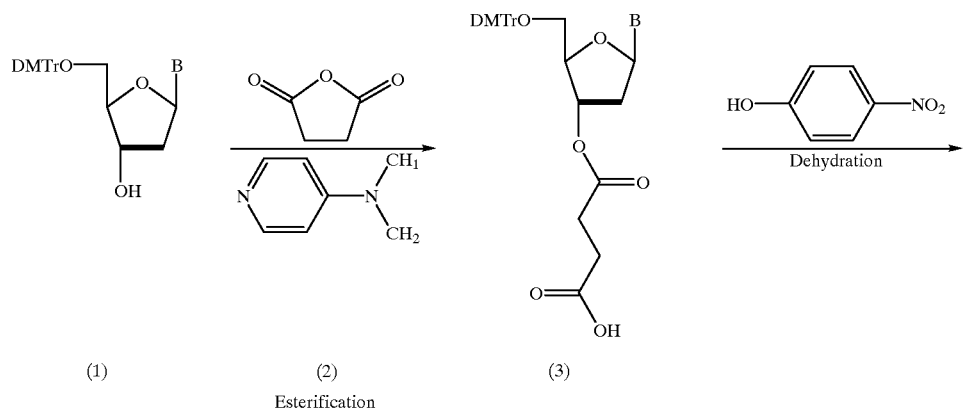

Esterification

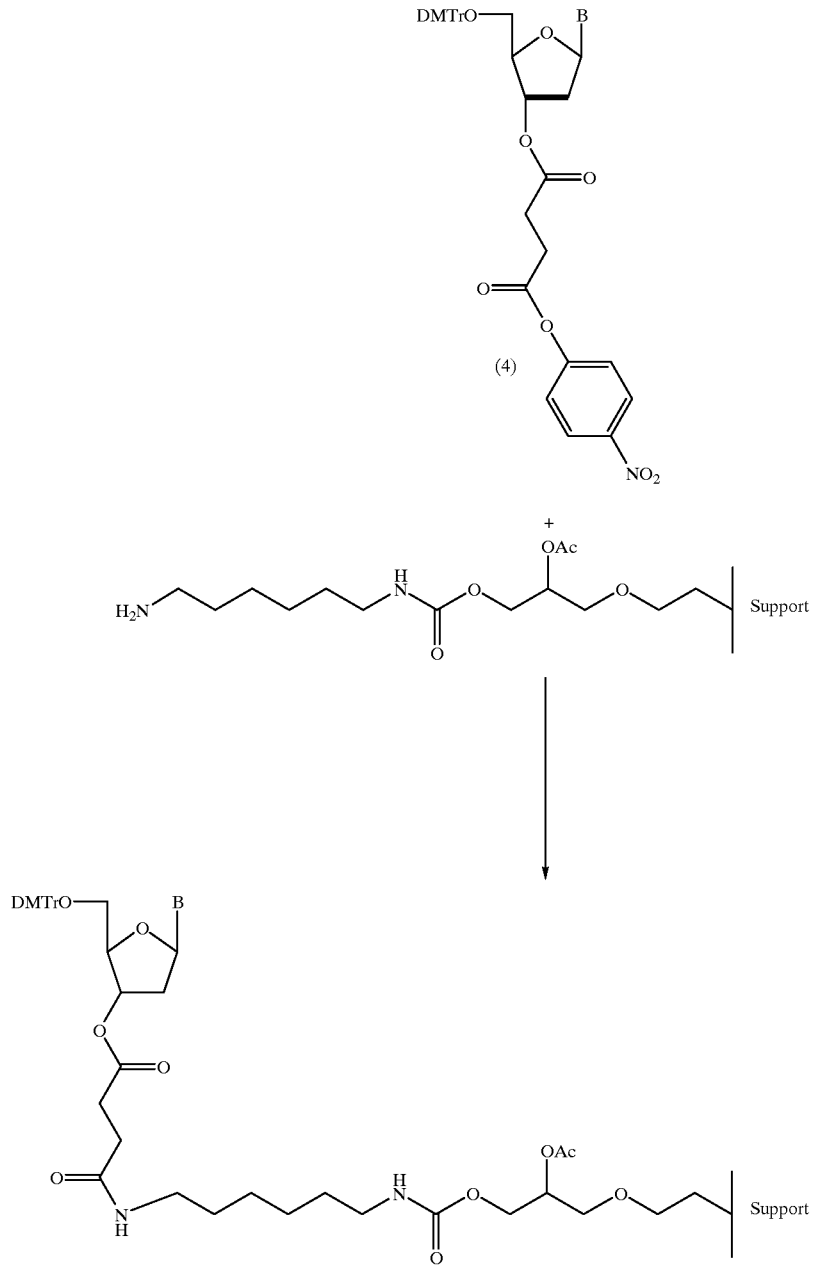

It should be noted that in the instance where a polymer containing both nucleoside and non-nucleoside monomer units is desired to be synthesized, a second or subsequent chemical species to be bonded to the first nucleoside can be any phosphoramidite-containing compound, such as for example, phosphoramidite-modified amines, thiols, disulfides, ethylene glycols and cholesterol derivatives. Such phosphoramidite-containing compounds are commercially available from Glen Research, Sterling, Va.

Hydrolyzing agents that can thus be used to cleave the oligonucleotide from the substrate are well known to those skilled in the art and include hydroxide ion (e.g., as an aqueous solution of sodium hydroxide), $CH_3NH_2$ or preferably, concentrated aqueous $NH_4OH$. In a preferred embodiment, the entire substrate to which the oligonucleotide, having phosphate groups, is bonded is rinsed with a solution of the hydrolyzing agent. Alternatively, the hydrolyzing agent can be dispensed as a microdroplet; in such a case, the microdroplet preferably comprises a high surface tension solvent.

Where the nucleoside, as the first chemical species, is attached to the substrate, or linker of the substrate, via an ester bond, it will be understood that prior to reaction with an additional nucleoside, the first added nucleoside is deprotected with a deprotecting agent which removes a protecting group from its 5' position. The subsequently dispensed nucleoside, having a phosphoramidite group at its 3' position, reacts with the nucleoside attached via the ester bond to the substrate or linker of the substrate, and having a deprotected hydroxyl group at its 5' position, to form a phosphite group. The resulting phosphite group is than treated with an oxidizing agent, described above, to form a phosphate group. Successive iterations of deprotection, treatment with a phophoramidite functionalized nucleoside, and oxidation, elongate the resulting oligonucleotide chain.

In a different specific embodiment, a linker, attaching the first chemical species' nucleoside unit to the substrate, contains a protease recognition site that, after synthesis of the oligonucleotide, is cleaved by use of the protease to release the substrate-anchored oligonucleotide. The entire substrate is preferably rinsed with a reaction mixture containing the protease; alternatively, the protease can be delivered as a microdroplet solution to the desired location on the substrate where the oligonucleotide is tethered.

The resulting cleaved oligonucleotide is preferably soluble in the solution of hydrolyzing agent or protease, as the case may be. Where the solution of hydrolyzing agent or protease, in which the substrate can be immersed, is contained in a vessel, the vessel will contain the cleaved oligonucleotide upon immersion of the oligonucleotide-anchored substrate into the hydrolyzing agent or protease solution. Methods for isolating and purifying the cleaved oligonucleotide are well known to those skilled in the art, and include, but are not limited to, gel electrophoresis and high-performance liquid chromatography.

The isolated and/or purified oligonucleotide obtained by the above methods can be used as known in the art, e.g., in hybridization assays, for expression analysis or genotyping; as sequencing or polymerase chain reaction (PCR) primers; or as templates for synthesis of oligonucleotide probes, etc.

It is to be understood that while the preferred method of synthesis of an oligonucleotide is in the 3'→5' direction, the present invention also provides methods for synthesizing oligonucleotides in the 5'→3' direction. Oligonucleotides produced having this direction are useful for enzymatic reactions, such as polymerization via DNA polymerase, while remaining attached to a substrate.

In the instance of synthesizing an oligonucleotide in the 5'→3' direction, a nucleoside having an hydroxyl protecting group at its 3' position, and a phosphoramidite at its 5' position, is attached to the substrate. Preferably, and alternatively, a nucleoside having an hydroxyl protecting group at its 3' position, and an activated O-succinate group at its 5' position is attached to the substrate. The nucleoside having an hydroxyl protecting group at its 3' position, and a phosphoramidite or an activated O-succinate group at its 5' position, is preferably applied to the substrate in a microdroplet of solution, preferably from an inkjet nozzle. Where the nucleoside has a phosphoramidite at its 5' position, the substrate used has an hydroxyl group, which reacts with the nucleoside's 5' phosphoramidite group to form a phosphite group, which can then be converted to a phosphate group. Where the nucleoside has an activated O-succinate group at its 5' position, the substrate used has an amino group, more preferably an amino group in the form of a long chain alkylamine, which reacts with the nucleoside's 5' activated O-succinate group to form an amide bond. Where the nucleoside has a phosphoramidite group at its 5' position, the esterification reaction between the phosphoramidite group and the hydroxyl group of the substrate is facilitated by a catalyst, as described above.

Once the nucleoside is anchored to the substrate, the 3' protecting group is removed as described above for the analogous 5' protecting group, preferably by rinsing the substrate with deprotecting agent, so as to expose a 3' hydroxyl group. Then, a second nucleoside having a phosphoramidite, preferably having a cyanoethyl group, at its 5' position, and having a protecting group at its 3' position, is dispensed, as a microdroplet of solution, at the locus of the substrate where the first nucleoside was added. Following dispensation of the second nucleoside, a catalyst, such as one described above, is dispensed, preferably as a microdroplet of solution, at the locus of the substrate where the second nucleoside was added, to facilitate coupling between the first and second nucleosides. The reaction between the 3' hydroxyl group of the first nucleoside and the 5' phosphoramidite group of the second nucleoside forms a phosphite group, which is oxidized as described above to form a phosphate group. Where the substrate has a hydroxyl group that reacts with a nucleoside's 5' phosphoramidite group, it may be desirable to "cap" remaining substrate hydroxyl groups, as described above, before proceeding to the subsequent steps.

Successive iterations of deprotection, dispensation of an additional nucleoside, dispensation of catalyst and oxidation steps, elongates the oligonucleotide chain. Then, as described above, the cyanoethyl groups of the resulting oligonucleotide are removed. Finally, the resulting oligonucleotide is hydrolyzed from the substrate, using a hydrolyzing agent described above.

In addition, the present invention provides syntheses of oligonucleotides having 5'-5' or 3'-3' linkages. Oligonucleotides having these linkages are useful for antisense and structural studies. Such oligonucleotides are obtained according to the general methods above, and using a combination of nucleosides having an hydroxyl protecting group at the 5' position and a phosphoramidite group at the 3' position, and vice versa. For example, a nucleoside having a deprotected hydroxyl group at its 5' position that is anchored to a substrate via the nucleoside's 3' group can react, preferably in the presence of a catalyst, with a second nucleoside having a phosphoramidite group at its 5' position and a protecting group at its 3' position, to form a 5'-5' linkage. The resulting phosphite group is oxidized to a phosphate group, and the protecting group from the second nucleoside's 3' position is removed. Similarly, a third nucleoside having a phosphoramidite group at its 3' position and a protecting group at its 5' position can react, preferably in the presence of a catalyst, with the exposed 3' hydroxyl group of the second nucleoside to form a 3'-3' linkage. Once the resulting phosphite group is oxidized to a phosphate group, the synthesis can be continued using a nucleoside having either a phosphoramidite group at its 5' position and a protecting group at its 3' position, or a phosphoramidite group at its 3' position and a protecting group at its 5' position, depending upon the type of linkage desired. Where it is desired that the resulting oligonucleotide be cleaved from its substrate, the substrate preferably has an amino group, more preferably an amino group in the form of a long chain alkylamine, that reacts with a first nucleoside that has an activated O-succinate group at its 3' position and a protecting group at its 5' position, or an activated O-succinate group at its 5' position and a protecting group at its 3' position.

In yet another embodiment, the invention provides a method for obtaining oligonucleotides, having 3'-5', 5'-3', 3'-3' or 5'-5' linkages, using the H-phosphonate method for oligonucleotide synthesis (see, for example, chapter 6 of J. F. Ramalho Ortigão et al., *Introduction to Solid-phase Oligonucleotide Chemistry* (http://www.interactiva.de/oligoman/intro_inh.html)). In this instance, where the oligonucleotide to be synthesized is ultimately sought to be cleaved from the substrate, a substrate having an amino group is reacted with a nucleoside having a protecting group at its 5' position and an activated O-succinate group at its 3' position, or having a protecting group at its 3' position and an activated O-succinate group at its 5' position; where the oligonucleotide is not to be subsequently cleaved from the support, the support can have an hydroxyl group, which is reacted, preferably in the presence of a catalyst, with a nucleoside having a protecting group at its 5' position and a phosphoramidite group at its 3' position, or having a protecting group at its 3' position and a phosphoramidite group at its 5' position. It is to be understood that the nucleoside reagents are delivered as microdroplets of solutions, preferably from inkjet nozzles.

Following removal of the protecting group, which exposes a reactive hydroxyl group, a second nucleoside, having an H-phosphonate salt group at its 5' position and a protecting group at its 3' position, or having an H-phosphonate salt group at its 3' position and a protecting group at its 5' position, is dispensed as a microdroplet solution at the locus of the support at which the first nucleoside was added. Useful H-phosphonate salts are those that are soluble in the solvents discussed in Section 5.2 above; preferably, the H-phosphonate salts are triethylammonium salts, or salts of 1,8-diazabicyclo[5.4.0.]undec-7-en (DBU). The reaction product of the H-phosphonate salts and the exposed hydroxyl group is an H-phosphonate diester.

Advantageously, the H-phosphonate salts react with the exposed hydroxyl group of the substrate-bound nucleoside in the presence of an activator which, without being bound to any particular theory, is believed to increase the electrophilicity of the H-phosphonate group. Suitable activators include but are not limited to acid chlorides, preferably pivaloyl chloride and 1-adamantane carbonyl chloride; and anhydrides, preferably dipentafluorophenyl carbonate. The activators can be dispensed as a microdroplet with the H-phosphonate salts as part of the same solution, or can be dispensed as separate microdroplets from separate solutions. Successive dispensations of H-phosphonate salt/activator solutions as microdroplets, or successive iterations of separate H-phosphonate salt and activator dispensation steps, elongates the resulting oligonucleotide chain.

Once the oligonucleotide has reached its desired length, the H-phosphonate diester linkages are oxidized using conventional reagents, preferably an aqueous iodine solution, to afford phosphate groups. The oxidizing agent can be dispensed as a microdroplet comprising a high surface tension solvent. Alternatively, the entire substrate to which the oligonucleotide is attached can be washed with the oxidizing reagent. The oligonucleotide can then be cleaved from the substrate according to methods described above.

In addition to the chemistries described above, alternative reactions can be used in the methods of the invention where oligomers comprising modified nucleosides or nucleoside derivatives are synthesized. Such modified nucleosides include, for example, combinations of modified phosphodiester linkages such as phosphorothioate, phosphorodithioate and methylphosphonate, as well as nucleosides having such modified bases such as inosine, 5'-nitroindole and 3'-nitropyrrole.

Synthesis of oligoribonucleotides, e.g., RNA, can similarly be accomplished using the present methods. Effective chemical methods for oligoribonucleotide synthesis have added complications resulting from the presence of the ribose 2'-hydroxyl group. However, ribonucleoside coupling chemistries and protecting groups are available and well known to those skilled in the art. Therefore, such chemistries are applicable to the methods described herein.

As with oligodeoxyribonucleotides described above, a range of modifications can similarly be introduced into the base, the sugar, or the phosphate portions of oligoribonucleotides, e.g., by preparation of appropriately protected phosphoramidite or H-phosphonate ribonucleoside monomers, and/or coupling such modified forms into oligoribonucleotides by solid-phase synthesis. Modified ribonucleoside analogues include, for example, 2'-O-methyl, 2'-O-allyl, 2'-fluoro, 2'-amino phosphorothioate, 2'-O-Me methylphosphonate, α-ribose and 2'-5'-linked ribonucleoside analogs.

In another preferred embodiment, the first chemical species is an amino acid; the second chemical species is a substrate having reactive functional groups, a linker attached to a substrate, or an amino acid or peptide attached to either the linker or directly to the substrate; and the third chemical species is an amino acid or a peptide chemically attached to either the linker or directly to the substrate. In this embodiment, the first chemical species is an amino acid having a protecting group on the carboxy group of its carboxy terminus, and the second chemical species is (a) a substrate, or a linker attached to a substrate, having an electrophilic group that is capable of forming a stable covalent bond with the amino group of the amino terminus of the amino acid, or (b) an amino acid or peptide attached to either the linker or directly to the substrate, and having a carboxy terminus that is capable of forming an amide bond with the amino group of the amino terminus of the amino acid. Alternatively and preferably, the first chemical species is an amino acid having a protecting group on the amino group of its amino terminus, and the second chemical species is (a) a substrate or a linker attached to a substrate having a nucleophilic group that is capable of forming a stable covalent bond with the carboxy terminus of the amino acid, or (b) an amino acid or peptide attached to either the linker or directly to the substrate, and having an amino terminus that is capable of forming an amide bond with the carboxy terminus of the amino acid. It will be understood that if the first chemical species and second chemical species bear additional reactive groups, those reactive groups can have additional protecting groups, so as to preclude unwanted side reactions with those groups if not protected.

Advantageously, where peptides are sought to be obtained, the reaction between the first chemical species and the second chemical species takes place in the presence of a catalyst; preferably, a stoichiometric amount of a catalyst such as dicyclohexylcarbodiimide or the like. In such a case the microdroplet solution can comprise the catalyst as well as the first chemical species.

Typically, a solution comprising an amino acid having a protecting group on the amino group of its amino terminus as the first chemical species and a stoichiometric amount of dicyclohexylcarbodiimide catalyst, is dispensed as a microdroplet onto a second chemical species, e.g., a substrate with a linker having, for example, hydroxyl functional groups, thereby forming a microdot containing an amino acid covalently bonded to the linker of the substrate via an ester bond as the third chemical species.

It is to be pointed out that suitable protecting groups for the amino group of the amino terminus of an amino acid include tert-butoxycarbonyl (tBOC) and 9-fluorenylmethoxycarbonyl (FMOC) protecting groups, and other protecting groups disclosed in Theodora W. Greene, *Protecting Groups in Organic Synthesis* 218–49 (1981), incorporated herein by reference.

The resulting N-protected amino acid that is covalently bonded to the linker of the substrate is then treated with a deprotecting agent that can remove the protecting group from the amino group of the amino acid's amino terminus: in the case where a tBOC protecting group is used, the deprotecting agent is an acid such as HCl or trifluoroacetic acid; in the case where an FMOC protecting group is used, the deprotecting agent is an organic base such as piperidine, morpholine or ethanolamine. The protecting group can be removed by immersing or otherwise washing the substrate in a bath or stream of a solution of the deprotecting agent. Alternatively, the deprotecting agent can be added, in the form of a microdroplet, onto the N-protected amino acid that is covalently bonded to the linker of the substrate. In such a case, the microdroplet preferably comprises a high surface tension solvent.

The resulting deprotected amino acid that is covalently bonded to the linker of the substrate, becomes the second chemical species relative to an impinging microdroplet of absolution of either the same or a different amino acid having a protecting group on the amino group of its amino terminus, and so on. The entire process is repeated until a peptide having a desired sequence or length is obtained.

It is to be pointed out that this process may be repeated at different loci of the substrate, using different first chemical species and second chemical species, so as to obtain, if desired, a different peptide at each loci.

The resulting peptide which is covalently attached to the linker of the substrate, and which has a protecting group on the amino group of its amino terminus, is treated, either via submersion of the substrate or via microdroplet impingement as described above, with a deprotecting agent that removes that protecting group and preferably all of the remaining protecting groups on the peptide, if any. If protecting groups remain on the peptide subsequent to treatment with the deprotecting agent, subsequent treatments with deprotecting agents can be effected until all of the protecting groups have been removed.

If desired, the resulting deprotected peptide synthesized by the above method can then be cleaved from the linker using conditions that will hydrolyze an ester bond in the presence of an amide bond, including treatment with mild hydroxide base, as well as other suitable conditions known to those skilled in the art.

The methods of the invention can be applied to other chemistries that rely on iterations of coupling and deprotection. For example, using the present methods, it is possible to construct arrays of other heteromeric polymers with sequence dependent properties.

It will be realized that a particular advantage of the method of the invention is that by keeping a record of the first chemical species dispensed, and accordingly third chemical species formed, at each of the microdot loci, libraries of chemical compounds having known sequences can be easily obtained. Such chemical compounds can have a variety of uses including, but not limited to, screening for biological activity whereby the respective chemical compound at each locus is exposed to a labeled or unlabeled nucleic acid or receptor, such as an antibody, a cell receptor, or any other variety of receptor.

Figure 5:
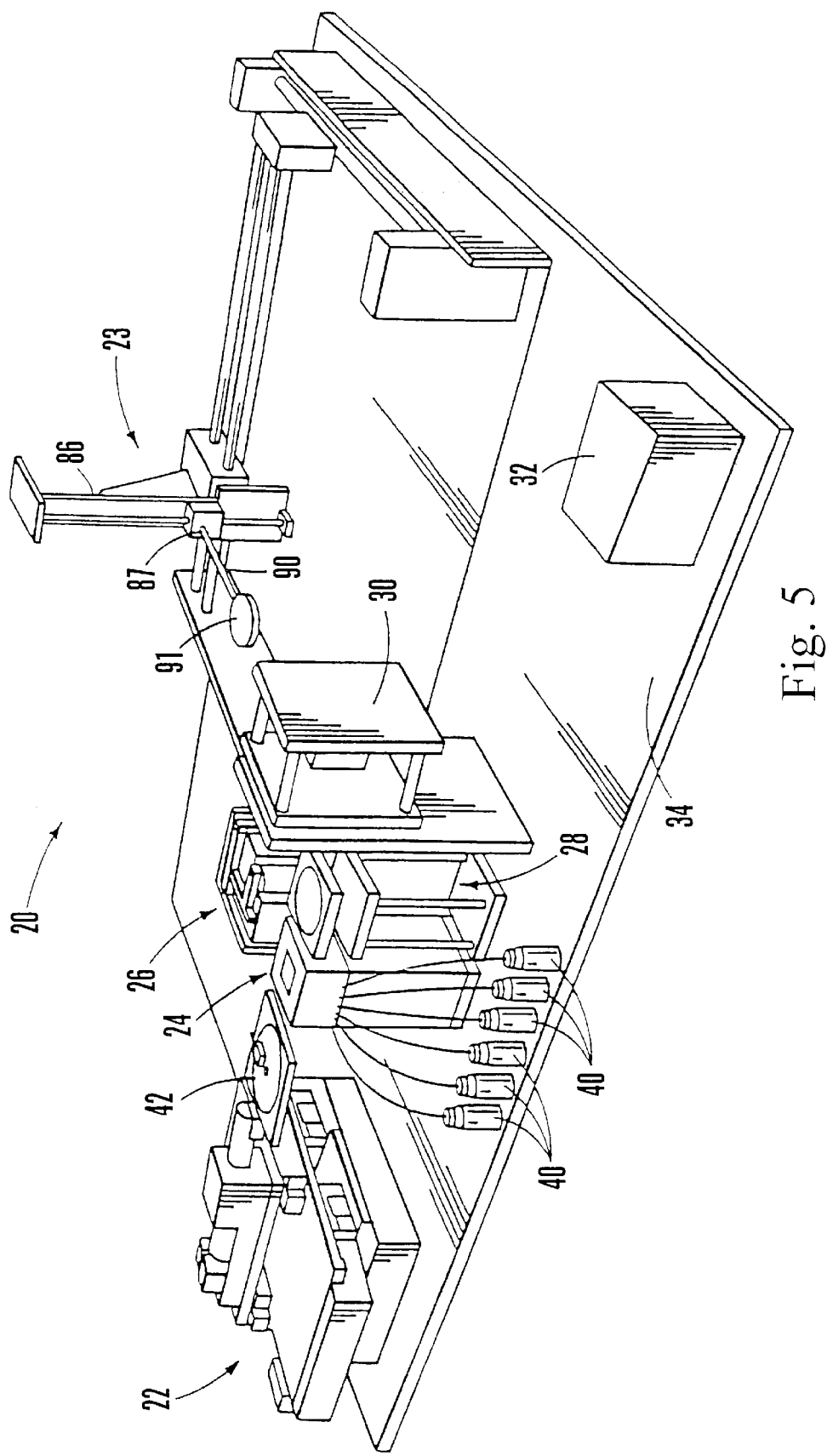
FIG. 5 shows an automated system for synthesizing oligonucleotides in accordance with the invention.

The following examples are presented by way of illustration and not by limitation on the scope of the invention.
Automated Synthesis System The methods of the invention for chemical synthesis using microdroplets are preferably automated. Preferably, the methods are automated as described below, using the exemplary apparatus and software as described herein.
System Implementation Shown in FIG. 5 is a preferred embodiment of an automated system for large-scale synthesis of biopolymers in accordance with the invention. As used herein, the term biopolymer is intended to mean any of numerous biologically occurring compounds which are synthesized from two or more individual monomer building blocks. Nucleic acids, polypeptides and carbohydrates are specific examples of biopolymers. The individual monomers for these biopolymers consist of nucleosides, amino acids and sugars, respectively. The term is intended to include natural and non-naturally occurring monomers as well as derivatives, analogues, and mimetics thereof.

The automated system is designated by reference numeral 20. Generally, system 20 comprises scanning transport 22, treating transport 23, a print head assembly 24, an alignment unit 26, a transfer station 28, a flow cell 30, and a substrate storage rack 32. The components are mounted, for example, on a base 34, and enclosed by a cover (not shown) so that processing can be performed in a dry nitrogen environment.

The components are used to manipulate a planar substrate and to synthesize biopolymers on the substrate under the automated control of a computer. The substrate used for the synthesis of two-dimensional biopolymer arrays is generally a wafer having a flat planar surface which has, or can be modified to have, reactive groups suitable for attaching further organic molecules. The substrate can additionally be porous so long as it supports the synthesis of biopolymer arrays. Specific examples of substrates useful in the automated system of the invention include glass, silica, silicon, polypropylene, TEFLON®, polyethylimine, nylon, fiberglass, paper and polystyrene. The surface can additionally consist of bead structures attached to a solid surface, wherein the beads are composed of one or more of the preceding materials. The dimensions of the substrate can vary and are determined to be complementary to the supporting structures of the automated system. The dimensions can be altered depending on the desired size and application of the array and the design of the supporting structures which hold the substrate.

The substrate is cycled once over the print head assembly to make a single deposit of a chosen biopolymer monomer at each desired site. In this single cycle, different sites can receive different monomers. For the synthesis of nucleic acid biopolymers, for example, any one of the four monomers is available for any particular site during any single print head cycle. A catalyst is applied by the print head to each substrate site after the monomers are deposited.

After a print head cycle, treating transport 23 is used to move the substrate from the print head assembly to flow cell 30, which "treats" the substrate by exposing it to selective fluids in order to rinse off unconnected monomers, oxidize, and deprotect the substrate. Once rinsed, the substrate is moved again to print head assembly 24 for a further cycle of monomer deposits, and then rinsed again in the flow cell. These steps are repeated numerous times to build desired biopolymer sequences. Different biopolymer sequences can be assembled at each site by using different sequences of monomers.

Inkjet printers generally employ print heads that may contain 50 to 100 independently controlled nozzles. With each nozzle operating at several hundred cycles per second (Hertz or Hz), a machine with five such print heads can deliver the appropriate reagents to 100,000 wells in a matter of seconds. A complete synthesis cycle can take, for example, 5 minutes, or just over 2 hours for an array of 100,000 biopolymers having 25 monomer residues. Print heads having more or less nozzles and which operate at different speeds can be used as well. Additionally, multiple print heads can be simultaneously used to synthesize the biopolymer arrays. Such configurations are known to those skilled in the art and will vary depending on the size, format and intended use of the array and the different reagents and monomers to be deposited.

Figure 6:
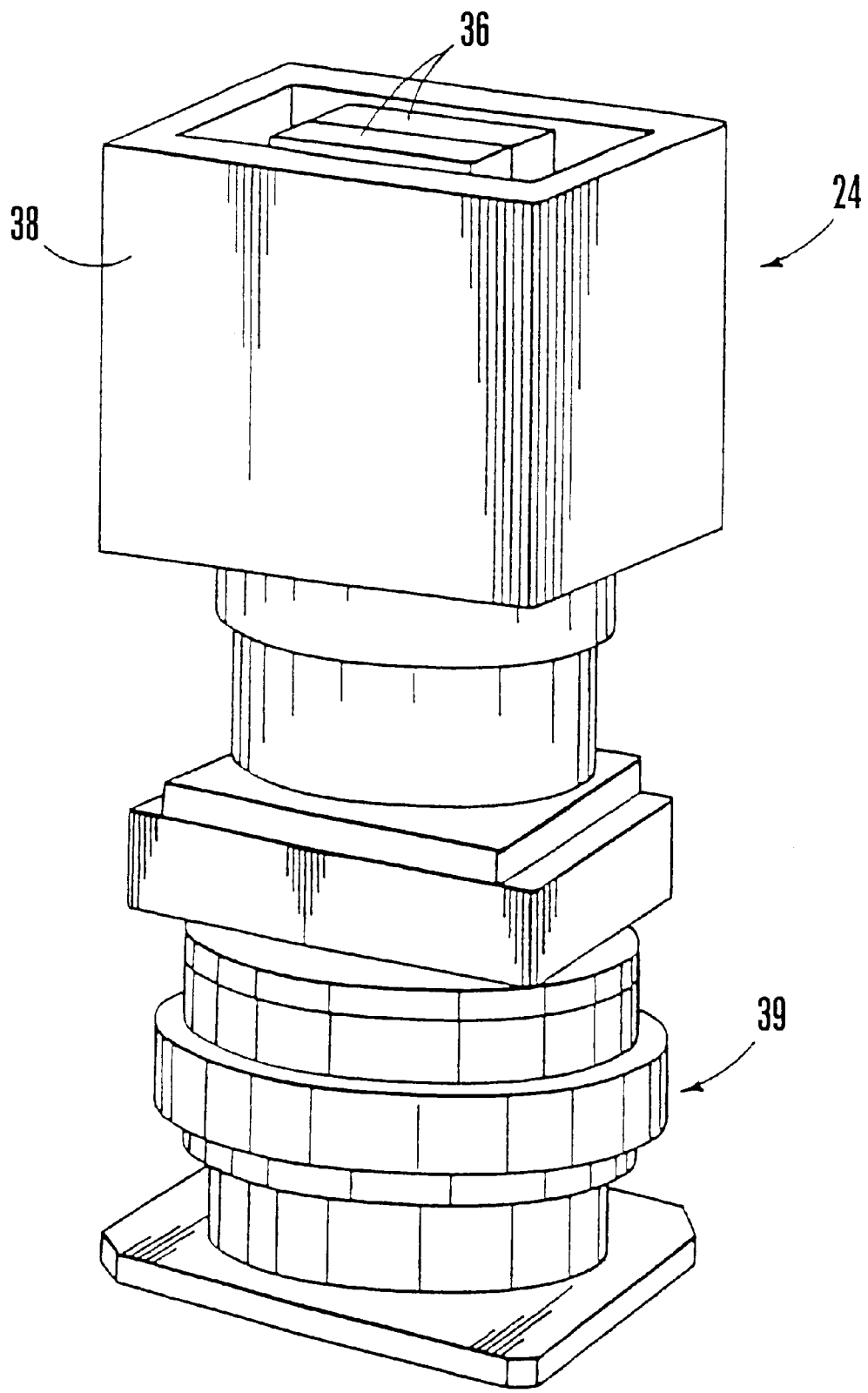
FIG. 6 shows inkjet print heads used in the system of FIG. 5.

FIG. 6 shows print head assembly 24. The print head assembly comprises two print heads 36, mounted within an aluminum block 38. The preferred print heads are inkjet print heads by Epson America, Inc., of Torrance, Calif., sold as spare parts for use in STYLUS COLOR II ink jet printers. These print heads are intended for use in depositing a pattern of ink droplets onto media positioned adjacent the print heads. More specifically, each print head comprises an array of 60 individual nozzles, which are piezoelectric pumps created with known etching techniques and formed with small cavities with narrow inlets and nozzles, as explained with respect to FIG. 3.

In this embodiment, the two print heads are aligned with each other and directed upwardly, to deposit liquid on a substrate that is positioned over the print heads. Block 38 and print heads 36 are supported on base 34 (FIG. 5) by calibration devices 39, which include adjustments for height, rotation, pitch, and yaw. Calibration devices 39 allow the print heads to be precisely aligned with the mechanism, described below, that positions substrates over the print head.

Each of the print heads has three separate fluid manifolds, attached to the manifold inlets. When combined, the two print heads have six manifolds, allowing the use of six different reagents. External reservoirs 40 (FIG. 5) are connected to supply reagents to the manifolds. Each print head has 60 nozzles organized as 3 banks of 20 nozzles. The 20 nozzles in a bank have a common reagent manifold. Each bank of nozzles is arranged linearly, along an axis that is perpendicular to the direction in which the substrate is to be moved across the print heads.

In the specific embodiment directed to the synthesis of nucleic acid biopolymers, four manifolds contain different nucleoside monomers as reagents. The monomers can be mixed with a catalyst such as 5-methylthiotetrazole, tetrazole, or preferably 5-ethylthiotetrazole, in advance or, alternatively, another manifold can be used to contain and apply the catalyst.

A complete synthesis cycle starts by delivering the appropriate nucleoside monomers along with a catalyst such as 5-ethylthiotetrazole to the substrate. After a layer of monomers are deposited on the substrate, the entire substrate is treated by rinsing off excess monomers, exposing the substrate to an oxidizing solution and then deprotecting for the next round of synthesis. The rinses are common to all the loci on the substrate and can be done, for example, by bulk immersion. One such cycle adds one monomer to each oligonucleotide, thus a substrate of oligonucleotides having a length of ten nucleosides requires 10 such cycles.

The number of cycles, and therefore, the length of the biopolymer will be determined by the need and desired use of the array. As such, the biopolymer lengths which can be achieved using the automated system of the invention are only limited by the types of reactive chemical species and existing coupling chemistries. For nucleic acid biopolymers, oligonucleotides of unlimited length, preferably between 10 and 100 monomers in length, and more preferably between 20 and 60 monomers in length, can routinely be synthesized.

For use in the automated synthesis system of the invention, the biopolymer monomers may be either dissolved in a solvent or, alternatively, the automated system can be adapted to contain a mixing reservoir to supply a solvent. Thus, in the automated system shown in FIG. 5, one or more of the external reservoirs 40 can contain a solvent or monomers dissolved in a solvent. The solvent is preferably a high surface tension solvent.

Figure 7:
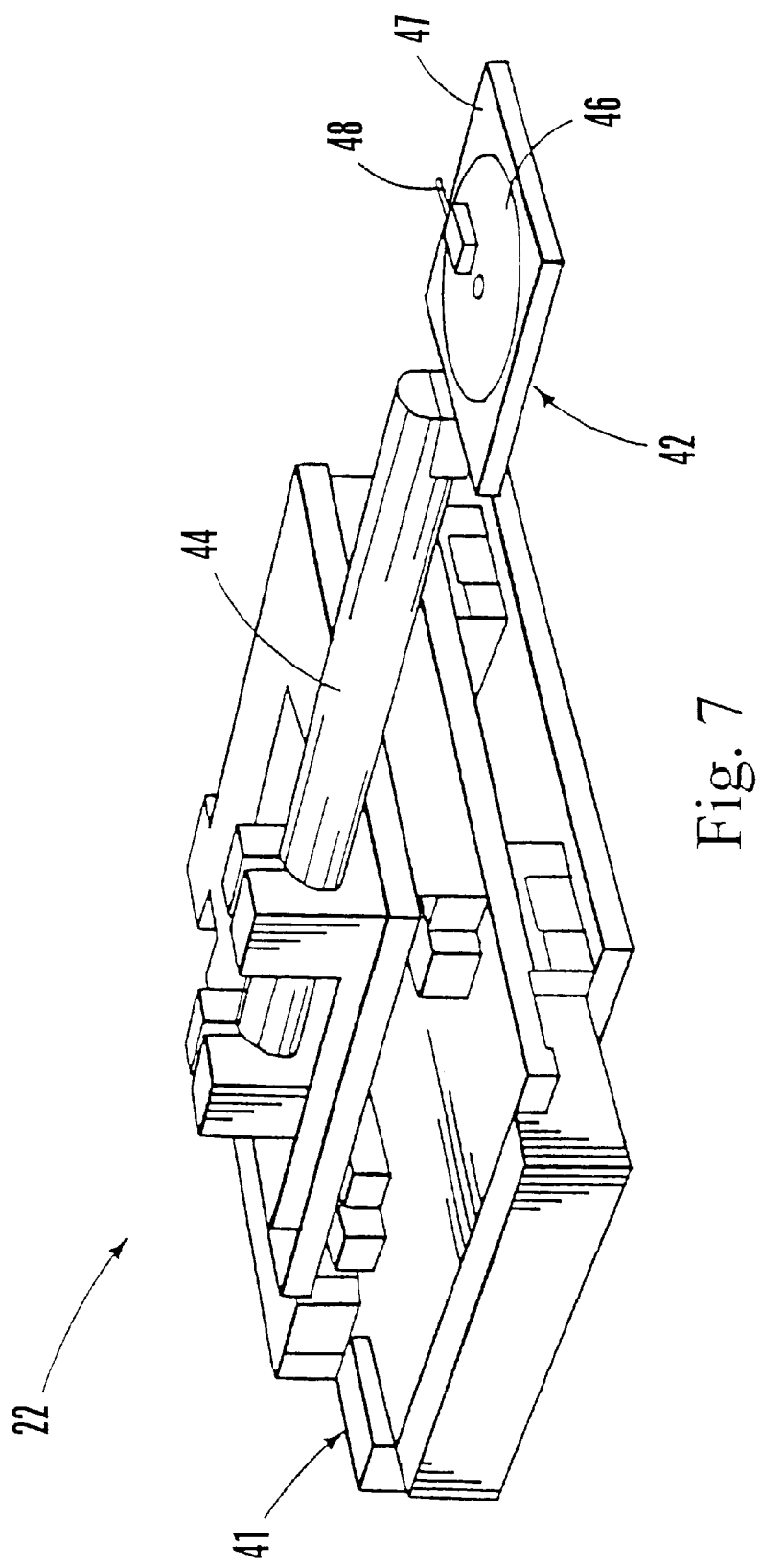
FIG. 7 shows a scanning transport used in the system of FIG. 5.

Scanning transport 22 is used to "scan" a substrate by moving the substrate over print head assembly 24 for depositing nucleoside monomers at specified loci or sites on the substrate. While print head control is accomplished in a manner similar to that commonly employed with inkjet printers, unlike in a standard inkjet printer the substrate is moved rather than the print head assembly itself. As shown in FIG. 7, the scanning transport comprises a translational stage having at least two axes of linear movement. More specifically, the scanning transport is an X-Y translation stage 41 oriented to provide two degrees of horizontal motion. Movement along each axis is accomplished by an electronic stepping motor that is geared to provide a linear resolution of about 5 $\mu$m. The preferred system uses an X-Y translation stage from Parker Hannifin Corp, Model 310062AT.

To hold the substrate, scanning transport 22 includes a vacuum chuck 42. Vacuum chuck 42 is mounted at the end of scanning arm 44 that extends laterally from X-Y translation stage 41. The vacuum chuck is connected relative to the X-Y translation stage so that the vacuum chuck can be moved back and forth and sideways over the print head.

The vacuum chuck includes a circular plate 46 having a planar lower surface with a plurality of interconnected concentric grooves (not shown). Vacuum is selectively applied to the interconnected grooves to hold the substrate to the lower surface of the vacuum chuck. To apply vacuum, a vacuum tube (not shown) extends to the grooves from an external vacuum source that is controlled by a solenoid valve (not shown). Circular plate 46 is mounted for rotation within a mated opening in substrate holder 47 that is in turn attached to a distal end of scanning arm 44. The opening preferably has a lower lip to support the circular plate 46 by its periphery from beneath. Clips (not shown) can be used to retain the circular plate in its mated opening, and to provide moderate friction that prevents accidental rotation of plate 46.

A small rotational adjustment pin 48 extends radially outward from the circular plate, beyond substrate holder 47. The rotational adjustment pin can be engaged to rotate circular plate 46 about a vertical axis.

The rotation feature of circular plate 46 is used to rotationally calibrate a substrate relative to the print head. No calibration is necessary for a substrate that is about to undergo its first print head cycle because initial positioning of the substrate with respect to the scanning transport is used to establish an initial pattern of synthesis sites on the substrate. During subsequent cycles, however, the substrate might be positioned differently on the vacuum chuck, requiring calibration steps. Horizontal position differences in position can be compensated for by translational stage 41 and its controlling electronics. Rotational misalignment (about the vertical z axis) is corrected by rotating circular plate 46 within its substrate holder 47. Specifically, the scanning transport 22 is moved to engage rotational adjustment pin 48 against a stationary vertical reference pin (not shown) mounted next to the alignment unit 26. In this fashion, rotating circular plate 46 can be rotated by an amount that restores its original rotational alignment.

Figure 8:
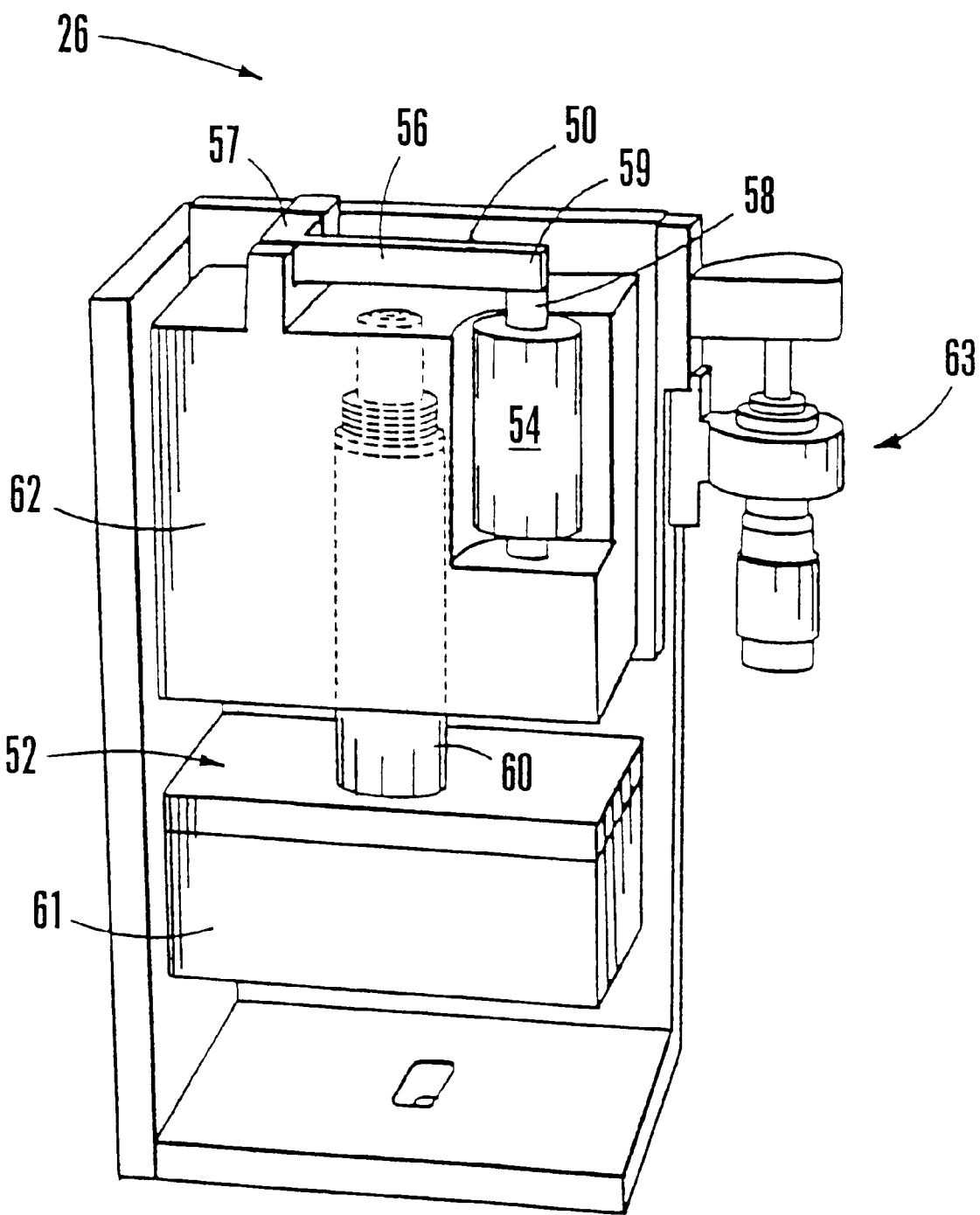
FIG. 8 shows an alignment unit used in the system of FIG. 5.

The amount of existing translational and rotational misalignment is determined by alignment unit 26. FIG. 8 shows this unit in more detail. Alignment unit 26 comprises a marker 50 and a camera 52. Marker 50 can be activated to establish marks at particular loci on the substrate for positionally calibrating the substrate relative to the scanning transport and to the print head assembly. It comprises a diamond tip or point that can be raised and lowered in response to activation and deactivation of a solenoid 54. When the marker is raised, it contacts an adjacent substrate. If the substrate is moved with respect to the marker, the marker scratches or scores the substrate, resulting in a visible line.

The marker is mounted at an intermediate position along a pivoting element 56 that is mounted at one end 57 for pivoting about a horizontal axis. Solenoid 54 has a vertically movable plunger 58 that engages the pivoting element at its other end 59.

Camera 52 comprises a lens unit 60 and a charged coupled device (CCD) imaging element 61 that are used to positionally calibrate the substrate relative to the scanning transport and to the print head assembly. Marker 50, pivoting element 57, solenoid 54, and camera 52 are mounted to a block 62 that can be adjusted vertically by means of a micrometer adjustment 63. This adjustment is used to focus the lens and CCD combination on an adjacent substrate. The preferred system uses a camera from Polaris Industries, Model MB-810B Micro Size CD.

In use, the initial positioning and alignment of a substrate is recorded by scoring two marks on the substrate. Preferably, a cross or X is made on two opposite ends or corners of the substrate. During subsequent handling of a particular substrate, each mark is positioned over lens 60 and its precise position is recorded. This information is used to calculate horizontal correction factors in the X and Y directions, and to calculate rotational misalignment. The horizontal correction factors are used when positioning the substrate over the print head with the scanning transport 22. The rotational misalignment is corrected by rotating circular plate 46 within its substrate holder 47 as described above.

Figure 9:
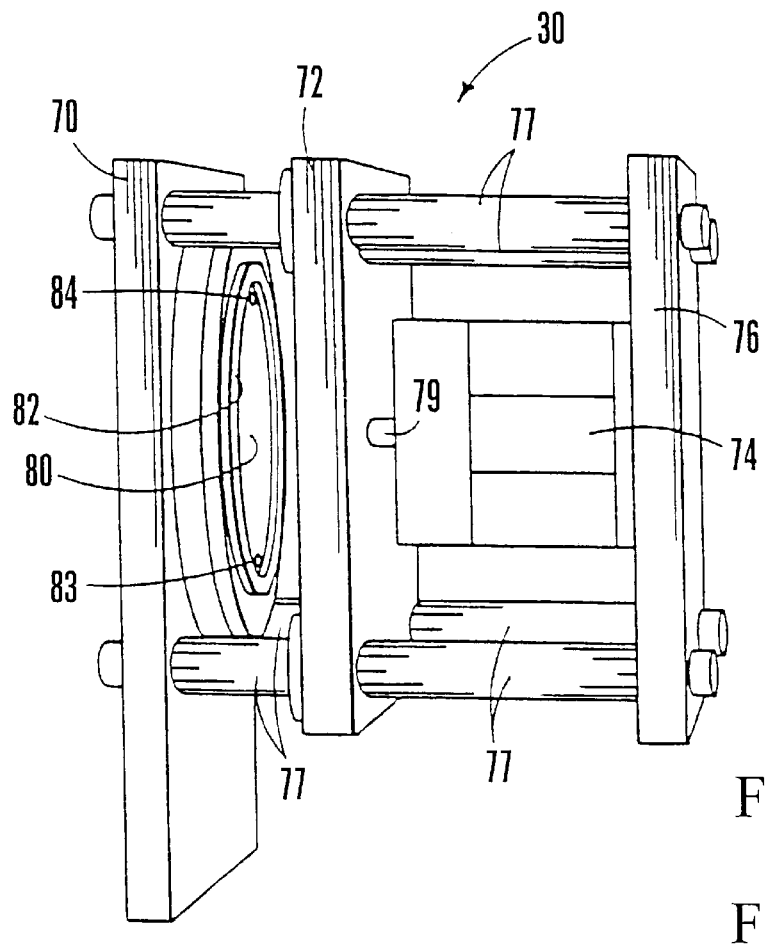
FIG. 9 shows a flow cell used in the system of FIG. 5.

FIG. 9 shows flow cell 30. Flow cell 30 is adapted for receiving the substrate and for "treating" the substrate by exposing the substrate to one or more selected reagents. Specifically, it is used for washing off unattached monomers, exposing the substrate to an oxidizing solution, and deprotecting the terminal nucleoside of the oligonucleotides being formed for the next round of synthesis.

In a preferred embodiment, flow cell 30 includes a rectangularly shaped stationary plate 70 mounted perpendicularly to base 34. A square backing plate 76 which is oriented parallel to stationary plate 70 is fixed to stationary plate 70 with four cylindrical rods 77. A square moving plate 72 that is parallel to and located between stationary plate 70 and backing plate 76 moves back and forth between these fixed plates guided by the rods 77. Each rod 77 fits through a hole located near a corner of moving plate 72. The holes are sized to rods 77 for a close sliding fit. One end of each rod 77 is fixed near a corner of backing plate 76. The other end of each rod 77 is fixed to stationary plate 70. When moving plate 72 moves toward stationary plate 70, a substrate is sandwiched between the two plates. Moving plate 72 is driven by a pneumatic cylinder 74 whose longitudinal axis is parallel to the direction of travel of moving plate 72. The base of pneumatic cylinder 74 is fixed to backing plate 76 and the end of piston rod 79 of pneumatic cylinder 74 is fixed to moving plate 72. Moving plate 72 is guided by the rods 77 to slide toward and away from stationary plate 70 in response to activation of pneumatic cylinder 74.

A vertical surface 80 of stationary plate 70 which faces moving plate 72 has a raised circular ring 82 made of a material that can withstand contact with the solvents used to treat the substrate. The raised circular ring 82 is sufficiently large in diameter to surround all portions of a substrate upon which reagents have been deposited. An inlet 83 extends through stationary plate 70 just inside the raised circular ring 82 at its lowermost portion and an outlet 84 extends through the stationary plate 70 just inside the raised circular ring 82 at its uppermost portion.

The planar surface of moving plate 72 facing stationary plate 70 has embedded in it a rubber o-ring (not shown) which protrudes above the surface of moving plate 72 and can press a substrate against raised circular ring 82. The rubber o-ring is the same diameter as the circular ring 82 so as to directly transfer pressure to the surface of the circular ring 82 and not to crack the substrate that is held between the o-ring and circular ring 82. A substrate so pressed against raised circular ring 82 forms a sealed chamber that is bounded by the surface of the substrate, by vertical surface 80, and by raised circular ring 82. The surface of the substrate forming a portion of the chamber can be exposed to various solvents by injecting such solvents into the chamber through inlet 83. The solvents exit the chamber through outlet 84. This aspect of the invention is automated by utilizing solenoid controlled valves in conjunction with solvent containers and appropriate tubing (not shown).

Treating transport 23 which is used for placing a substrate within the flow cell 30 comprises an X-Y translation stage, an elevator 86 that provides vertical (Z axis) movement, and a rotator 87 to provide motorized rotational movement about the longitudinal axis of an elongated rod 90 which extends from rotator 87. Movement along each of the X, Y, Z, and rotational axes is controlled by a stepping motor. The treating transport 23 also includes a vacuum chuck 91 which is attached to the end of the elongated rod 90 distal from the rotator 87. The vacuum chuck 91 has a circular shape that is approximately the size of the substrate upon which synthesis is being performed. The vacuum chuck 91 is thus configured to hold the surface of the substrate away from the surface on which reagents are being deposited. The vacuum chuck 91 is relatively thin so that it can be positioned conveniently between stationary plate 70 and moving plate 72 of flow cell 30. By controlling the X-Y translation stage, the elevator 86, and the rotator 87, vacuum chuck 91 can be moved along two horizontal axes and a vertical axis, and can also be rotated about one of the horizontal axes.

When vacuum chuck 91 positions a substrate between circular ring 82 and the surface of moving plate 72, a low vacuum of approximately three feet of water (1.3 pounds per square inch) is created within the chamber formed by the substrate, vertical surface 80, and circular ring 82. This slow vacuum holds the substrate in place after the vacuum chuck 91 retracts and before moving plate 72 moves in to firmly press the substrate against circular ring 82.

Figure 10:
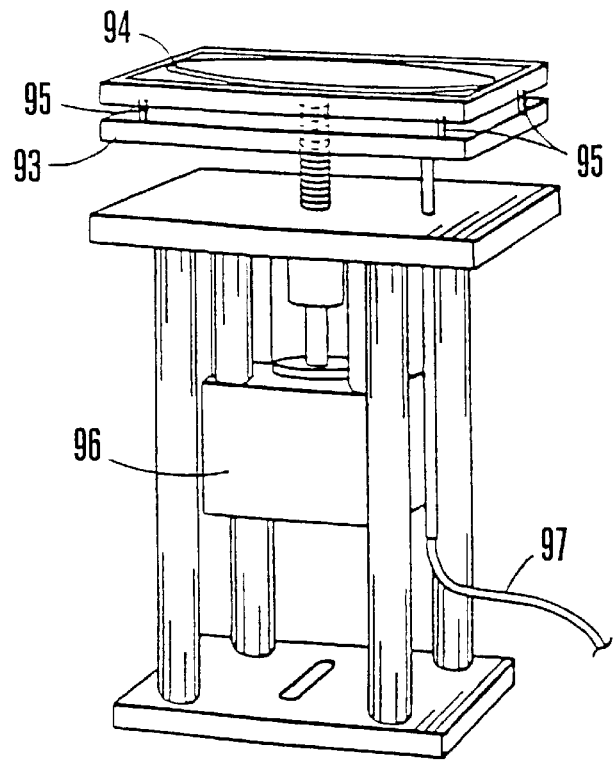
FIG. 10 shows a transfer station used in the system of FIG. 5.

Transfer station 28, shown in more detail in FIG. 10, serves an intermediate holding location for the substrate when the substrate is transferred between scanning transport 22 and treating transport 23. Transfer station 28 includes a planar motorized platform 93 oriented parallel to base 34 that supports a planar vacuum chuck 94. Vacuum chuck 94 has a square upper surface oriented parallel to motorized platform 93 upon which a substrate can rest. Vacuum is applied about the periphery of the upper surface of vacuum chuck 94 to secure the substrate when the substrate is placed on vacuum chuck 94.

Vacuum chuck 94 is supported on top of motorized platform 93 by four coil springs 95 which are located between the motorized platform 93 and the vacuum chuck 94. One coil spring 95 is positioned near each of the corners of vacuum chuck 94. Motorized platform 93 can be raised and lowered by a stepping motor 96 which is located below motorized platform 93. Vacuum is communicated to vacuum chuck 94 by a vacuum line 97, which communicates the vacuum by a solenoid controlled valve (not shown). To receive a substrate held by vacuum chuck 42 of scanning transport 22, the motorized platform 93 is raised until the upper surface of vacuum chuck 94 contacts the lower surface of the substrate. Motorized platform 93 does not have to move vertically to transfer a substrate to or from vacuum chuck 91 of treating transport 23 since that mechanism has vertical movement capability. Coil spring 95 absorbs any over-travel of motorized platform 93. Once the substrate has been grasped by vacuum chuck 94, motorized platform 93 is lowered.

Figure 11:
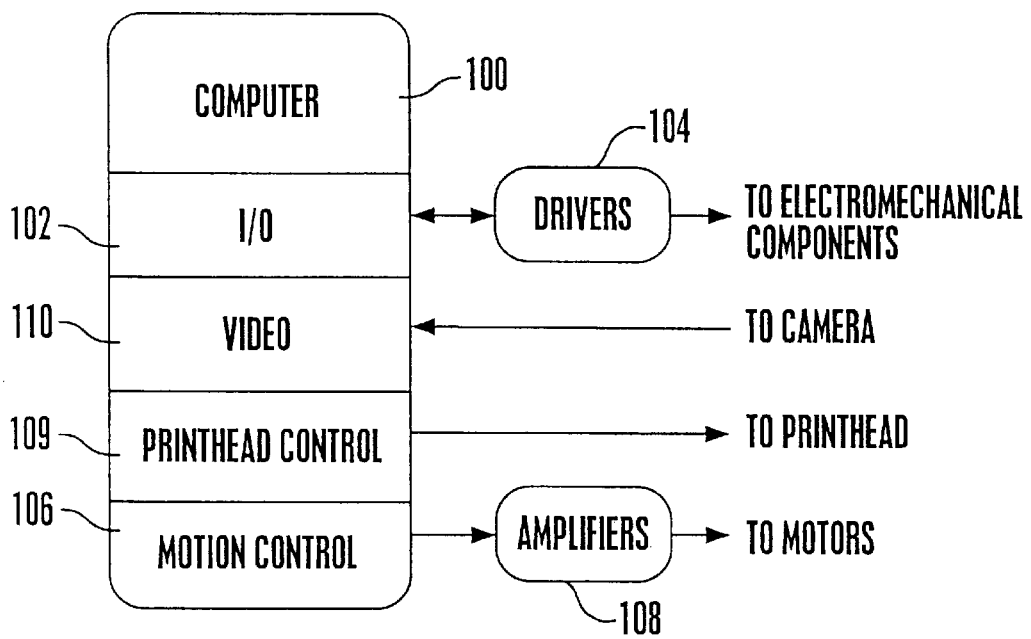
FIG. 11 is a block diagram showing a computer and control components used in conjunction with the system of FIG. 5.

FIG. 11 shows control components used to manipulate the various electromechanical components described above. Such components include a computer 100 having a microprocessor and associated memory components such as electronic memory and mass storage devices. The preferred system uses an IBM-compatible computer. Computer 100 includes common user interface components such as a monitor, a keyboard, and a mouse. The computer also has an expansion bus allowing various specialized peripheral devices and interfaces to be used in conjunction with the computer.

Various electronic hardware is provided for use in conjunction with computer 100 for actuating solenoids, stepping motors, and other components that control the physical operation of the hardware described above. Some of these components are implemented on expansion cards that are plugged directly into the expansion bus of computer 100, while other components are external to computer 100. The specific design and configuration of these electronic components will vary depending upon the particular electromechanical components used. As an example, the control components of FIG. 11 include a digital I/O card 102 having a plurality of digital inputs and outputs. This card is plugged directly into the expansion bus of computer 100. External driver circuits 104 are used as a buffer between the computer-level signals of I/O card 102 and the higher level signals used by the electromechanical components themselves. Solenoids are controlled with outputs from I/O card 102.

A frame capture circuit 110 is plugged into the expansion bus of computer 100. Frame capture circuit 110 receives a video signal from camera 52 and provides a two-dimensional array of pixel values for use by computer 100. Frame capture circuit 110 and the digital image it produces are used to locate the substrate marks made by marker 50 and to thereby determine any necessary compensation in positioning the substrate with respect to the print head. The preferred system uses a frame capture circuit on a WinVision Video capture board from Quanta Corp.

A plurality of motion control cards 106 are also plugged into the expansion bus of computer 100. These are conventional stepping motor control cards that operate in conjunction with computer 100 to control movements of the various stepping motors described above. The preferred system uses motion control cards from Oregon Micro Systems Inc., Model PC34-4. External driver circuits or amplifiers 108 are electrically connected between the motion control cards and the stepping motors themselves.

A print head controller 109 is also plugged into the expansion bus of computer 100. This circuit has electrical drivers that are configured specifically for the particular print heads that are chosen for use in print head assembly 24. In many cases, it will be necessary for these drivers to receive position feedback signals from the motion control circuits controlling the scanning transport 22, in order to coordinate print head firing with progress of the substrate across the print head assembly.

Figure 12:
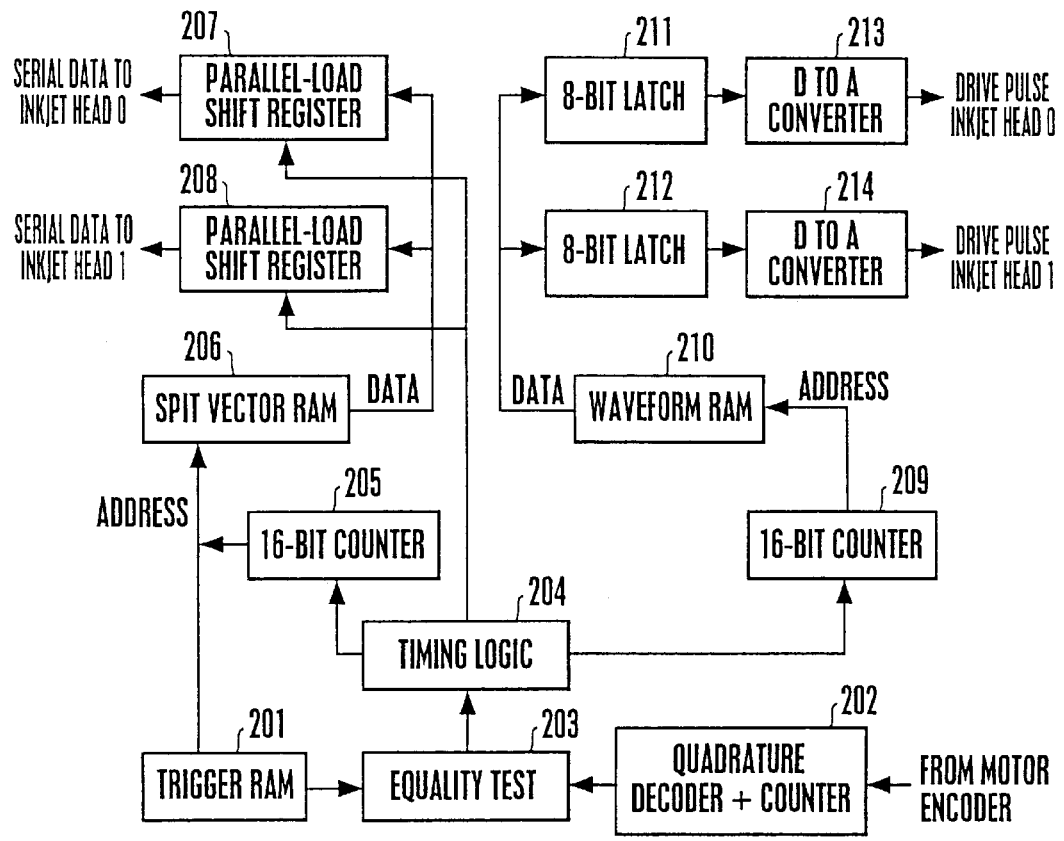
FIG. 12 is a block diagram of a controller used to control the inkjet print heads.

FIG. 12 shows in detail printer head controller 109 for controlling the inkjet printer heads. Trigger RAM 201 stores X-positions of the substrate where the deposition is to take place. Quadrature decoder & counter 202 produces the current X-position of the substrate by decoding the signal from a stepping motor used to move the substrate. Equality test 203 compares the current X-position with the X-position of deposition and produces a match signal. The match signal is provided to timing logic 204, which generates various timing signals to synchronize the activities across the components. Timing logic 204 uses 16-bit counter 205 to generate address signals to access the trigger RAM 201 as well as spit vector RAM 206. The spit vector RAM 206 stores a bit map for each trigger point where each bit represent the activation of a nozzle. The bitmap is loaded to each head using parallel-load shift registers 207 and 208. Timing logic 204 also uses 16-bit counter 209 to generate an address signal to access waveform RAM 210, which contains data representing the electric pulse waveform supplied to the print head. The waveform data are loaded to 8-bit latches 211 and 212 and converted to pulse signals using digital-to-analog (D-to-A) converters 213 and 214.

Computer 100 is programmed using conventional programming techniques to control movement of the various moving parts described above. Other types of computers or control logic could of course be used in place of the computer described. For example, an industrial-control computer unit referred to as a programmable controller might be substituted in place of a desktop computer.

Computer 100 is programmed specifically to move substrates between rack 32 and the two processing components: print head assembly 24 and flow cell 30 with respect to a single substrate, a first step might comprise retrieving the substrate from rack 32 with treating transport 23 and moving the substrate to transfer station 28. Rack 32 has slots for receiving and storing substrates in vertical orientations. Other orientations can be equally substituted. Since substrates are stored vertically in rack 32, vacuum chuck 90 of treating transport 23 is turned to a vertical orientation and moved adjacent the rear surface of the substrate. Vacuum is applied to vacuum chuck 91 by activating a solenoid valve, and vacuum chuck 91 is withdrawn from rack 32 along with the substrate.

Vacuum chuck 91 is then rotated to a horizontal orientation and moved to a position over transfer station 28. Vacuum chuck 91 is lowered to place the substrate on vacuum chuck 94. Vacuum is applied to vacuum chuck 94 of transport station 28 by activating a solenoid valve. The vacuum is disconnected from vacuum chuck 91.

Vacuum chuck 42 of scanning transport 22 is then moved over the substrate, and the substrate is raised by transfer station 28 so that it engages vacuum chuck 42. Vacuum is applied to vacuum chuck 42 by activating a solenoid valve.

If this is the initial cycling of the substrate, it is moved over marker 50 to establish one or more calibration marks on the substrate as already described. The substrate is then moved over print head assembly 24.

If the substrate has already been cycled over the print head, the substrate is moved over camera 52 while computer 100 performs a step of locating the marks in conjunction with the camera. Accordingly, each mark is located individually. That is, one of the two marks is positioned within the camera's field of view and an image is acquired by computer 100. This is repeated with the other mark. Using the two acquired images that include the marks, the computer determines the position of the substrate relative to X-Y translation stage 41 and in relation to its initial position as represented by the marks. The computer then performs a software calibration of X-Y translation stage 41 to account for any difference in the position of the substrate in comparison to its original position.

The computer also determines the rotational misalignment of the substrate with reference to the marks, again using the acquired images. In response to any rotational misalignment, the computer moves X-Y translational stage 41 to engage rotational adjustment pin 48 of the vacuum chuck 42 with the vertical reference pin to rotate the circular plate 46 of vacuum chuck 42 by an angular displacement that corrects for the misalignment.

Once the substrate has been positionally calibrated, the computer moves the substrate over print head assembly 24 with scanning transport 22 while simultaneously firing print head 36 repeatedly to deposit the nucleoside monomers at appropriate sites. Multiple passes might be required to reach all the sites of the substrate. Further passes are made to apply a catalyst. The computer then moves the substrate to transfer station 28 with scanning transport 22. Treating transport 23 is then moved to transfer station 28 to pick up the substrate. Vacuum chuck 91 of treating transport 23 carries the substrate to flow cell 30 and positions it therein. A low vacuum of approximately three feet of water (1.3 pounds per square inch) is applied to the chamber formed by the substrate, vertical surface 80, and circular ring 82. This low pressure holds the substrate in place while the vacuum chuck 91 retracts. Moving plate 72 then clamps the substrate firmly in the flow cell 30. Rinsing solvents are then cycled through flow cell 30. The substrate is then released from the flow cell. If processing is complete, treating transport 23 moves the substrate back to rack 32. Otherwise, the steps above are repeated.

Software Implementation

Flow charts detailing the operation of the software controlling the automated system are depicted in FIGS. 13–21. Here, while "wafer" is used to describe a specific example of a substrate, it will be clear that other substrates may also be used.

Figure 13:
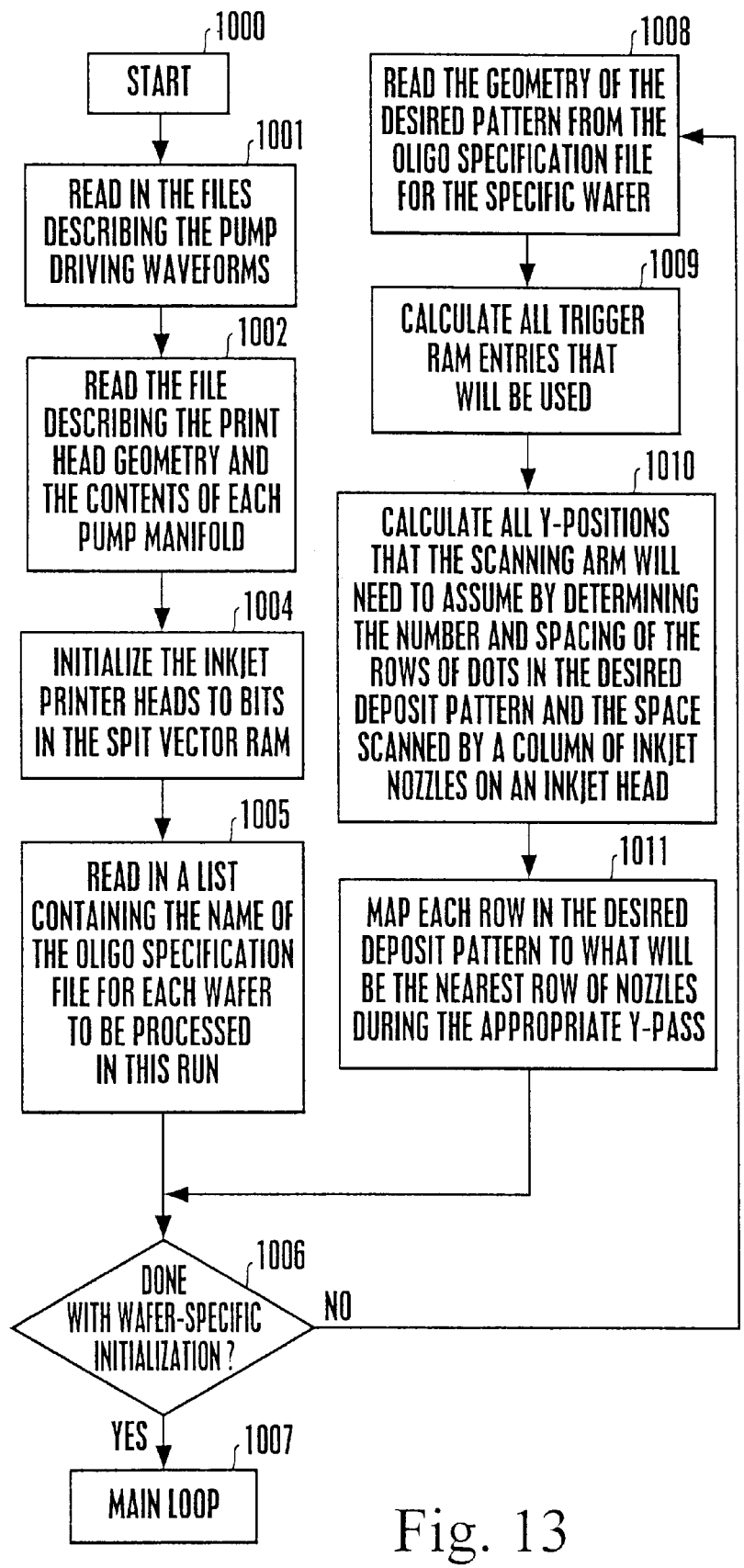
FIG. 13 is a flow chart depicting the operation of the computer software used to initialize the inkjet print heads.

FIG. 13 shows in detail the steps for the initialization of the program. After the program starts at step 1000, it reads in the file storing the pump driving waveforms describing voltage waveforms for activating the piezoelectric pumps in the inkjet print head (step 1001). Next, the program reads in the file describing the print head geometry describing how the nozzles in the print head are spaced and the contents of each manifold connected to the nozzles (step 1002). Next, the program initializes the mapping from individual nozzles on the inkjet print heads to bits in the spit vector RAM (step 1004). The program then reads in a list containing the name of an oligo specification file storing the geometry of the desired pattern to be deposited in a particular wafer to be processed in a particular run (step 1005).

If the program is done with wafer-specific initialization, it proceeds to the main loop in step 1007. Otherwise, the program reads the oligo specification file storing the geometry of the desired pattern to be deposited in a particular wafer (step 1008). The program then calculates all trigger RAM 201 entries that will be used, which include a distinct inkjet nozzle trigger point (X-location) and a distinct column of dots in the pattern on a wafer at each trigger point (step 1009). The program then calculates all Y-positions (passes) that the scanning arm will need to make in the course of synthesizing one layer of nucleoside monomers (step 1010). During the operation, the scanning arm moves to Y-positions, then sweeps across the X-positions required to trip all the desired trigger points. The required Y-positions are determined by the number and spacing of the rows of dots in the desired pattern and the space spanned by a column of inkjet nozzles on an inkjet print head. The program also determines the number of times the trigger RAM 201 will need to be reloaded while scanning one layer of nucleoside monomers. The program maps each row in the directed wafer pattern to what will be the nearest row of nozzles during the appropriate Y-pass (step 1011).

Figure 14:
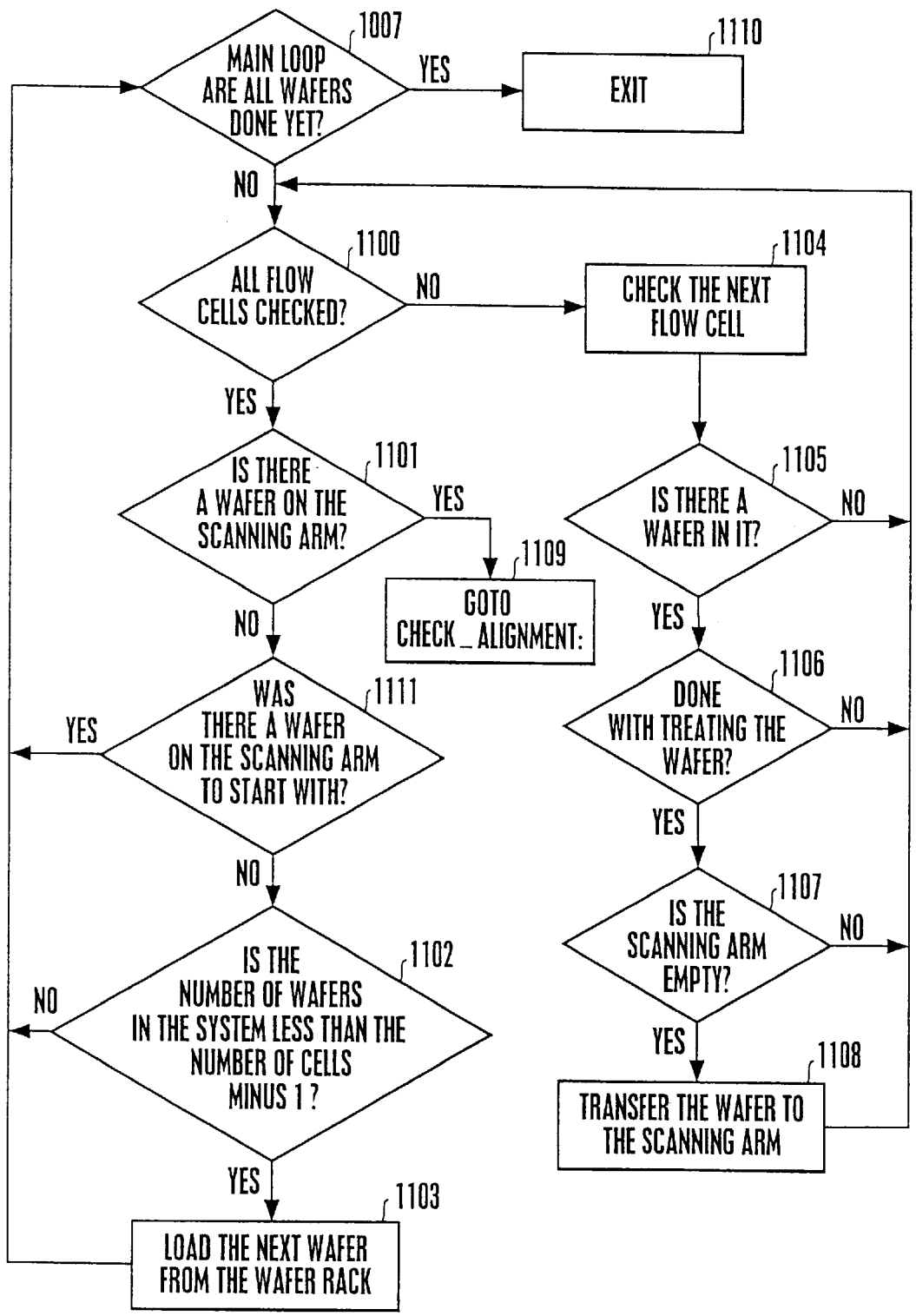
FIG. 14 is a flow chart depicting the operation of the software used to control the operation of the automated synthesis system.

FIG. 14 shows the main loop involving the operation of the automated synthesis system. In the case where there are multiple flow cells, the program first determines whether all flow cells were checked (step 1100). If they were not, it checks each flow cell to see whether it is done with treating the wafer (steps 1104–1106). If the treatment is done, the wafer is transferred to scanning 44 arm if the scanning arm is empty.

If all the flow cells were checked, the program checks whether there is a wafer on the scanning arm (step 1101). If there is, it proceeds to the Check_Alignment routine (step 1109) where it does initial positioning and alignment of the wafer. If there is no longer a wafer on the scanning arm (i.e., it was removed during the Check_Alignment routine) or there wasn't to start with (step 1111), the program checks whether the number of wafers in the system is less than the number of flow cells minus 1, i.e.:, whether all the flow cells are not full. If all the flow cells are not full, the system loads the next wafer from wafer rack 32 (steps 1102–1103).

Figure 15:
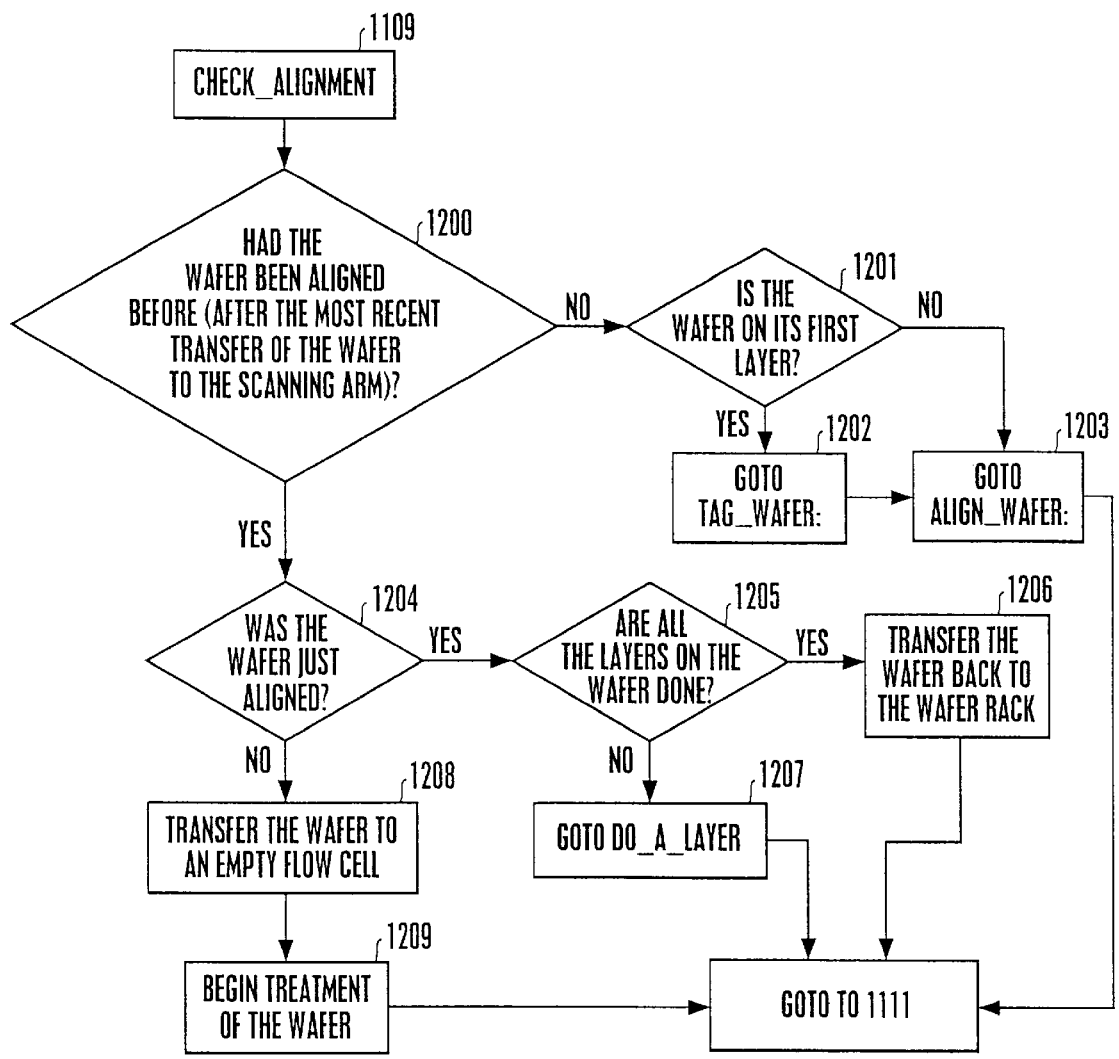
FIG. 15 is a flow chart depicting the operation of the software used to control the operation of the scanning transport and the operation of the flow cell.

FIG. 15 shows the Check_Alignment routine in detail. The program checks whether the wafer had been aligned previously (step 1200) after its most recent transfer to the scanning arm. If so, the program checks whether the wafer is to receive the first layer of deposition (step 1201). If it is, the program executes a routine for "tagging" the wafer, i.e., making registration marks for subsequent re-alignment (step 1202), which will be described in more detail with reference to FIG. 12. The program then executes a routine for aligning the wafer (step 1203), which will also be described in more detail with reference to FIG. 12.

If the wafer had been aligned before, the program checks whether the wafer has been just aligned (step 1204). If so, the program checks whether all the layers on the wafer are done (step 1205). If so, the wafer is transferred back to the wafer storage rack (step 1206). Otherwise, the program executes the Do_a_layer routine for depositing a layer on the wafer (step 1207). If the wafer has not been just aligned, i.e., the deposition has just been finished, the wafer is transferred to an empty flow cell (step 1209) and the treatment of the wafer starts (step 1209).

Figure 16:
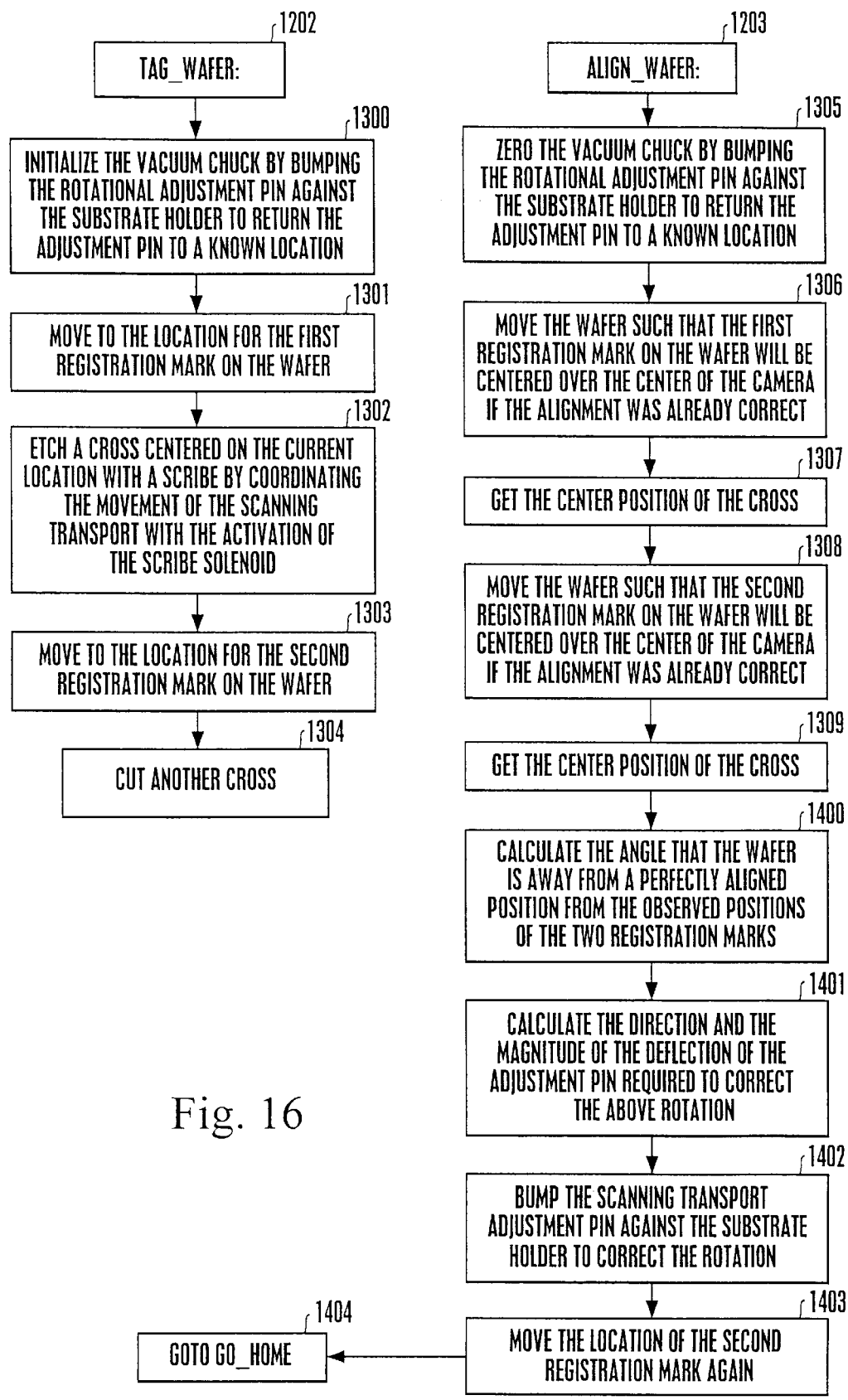
FIG. 16 is a flow chart depicting the operation of the software used to align a substrate relative to the print heads.

FIG. 16 shows in detail the routine for tagging the wafer and the routine for aligning the wafer.

The routine for tagging the wafer by scoring registration marks consists of steps 1300–1304. The rotational position of vacuum chuck 42 is initialized by bumping rotational adjustment pin 48 against the vertical reference pin to return the adjustment pin to a known location (step 1300). The scanning arm moves the wafer to a location for the first registration mark on the wafer (step 1301). A cross is cut on the wafer by coordinating the movement of the scanning arm with the activation of solenoid 54 for raising the scribe tip (step 1302). Scanning arm 44 moves the wafer to another location for the second registration mark (step 1303). Another cross is cut on the wafer (step 1304).

The routine for aligning the wafer once the registration marks are scored on the wafer consists of steps 1305–1404.

Vacuum chuck 42 is initialized by bumping rotational adjustment pin 48 against the vertical reference pin to return the adjustment pin to a known location (step 1305). Scanning arm 44 moves the wafer such that the first registration mark will be centered over the center of camera 52 if the alignment was already correct (step 1306). This should place the registration mark somewhere in the camera's field of view. The center position of the cross of the first registration mark is measured (step 1307). Scanning arm 44 moves the wafer such that the second registration mark on the wafer will be centered over the center of the camera if the alignment was already correct (step 1308). The center position of the cross of the second registration mark is measured (step 1309). The program calculates the angle that the wafer is rotated away from a perfectly aligned position from the measured positions of the two registration marks (step 1400). The program then calculates the direction and the magnitude of the deflection of rotational adjustment pin 48 required to correct the above rotation (step 1401). The rotational adjustment pin is bumped against the vertical reference pin to correct the rotation (step 1402). The scanning arm moves the wafer so that the second registration mark is now over the center of the camera (step 1403). The program executes the Go_home routine for calculating the X and Y-position adjustments such that the center of the registration mark is located directly over the center of the camera (step 1404).

Figure 17:
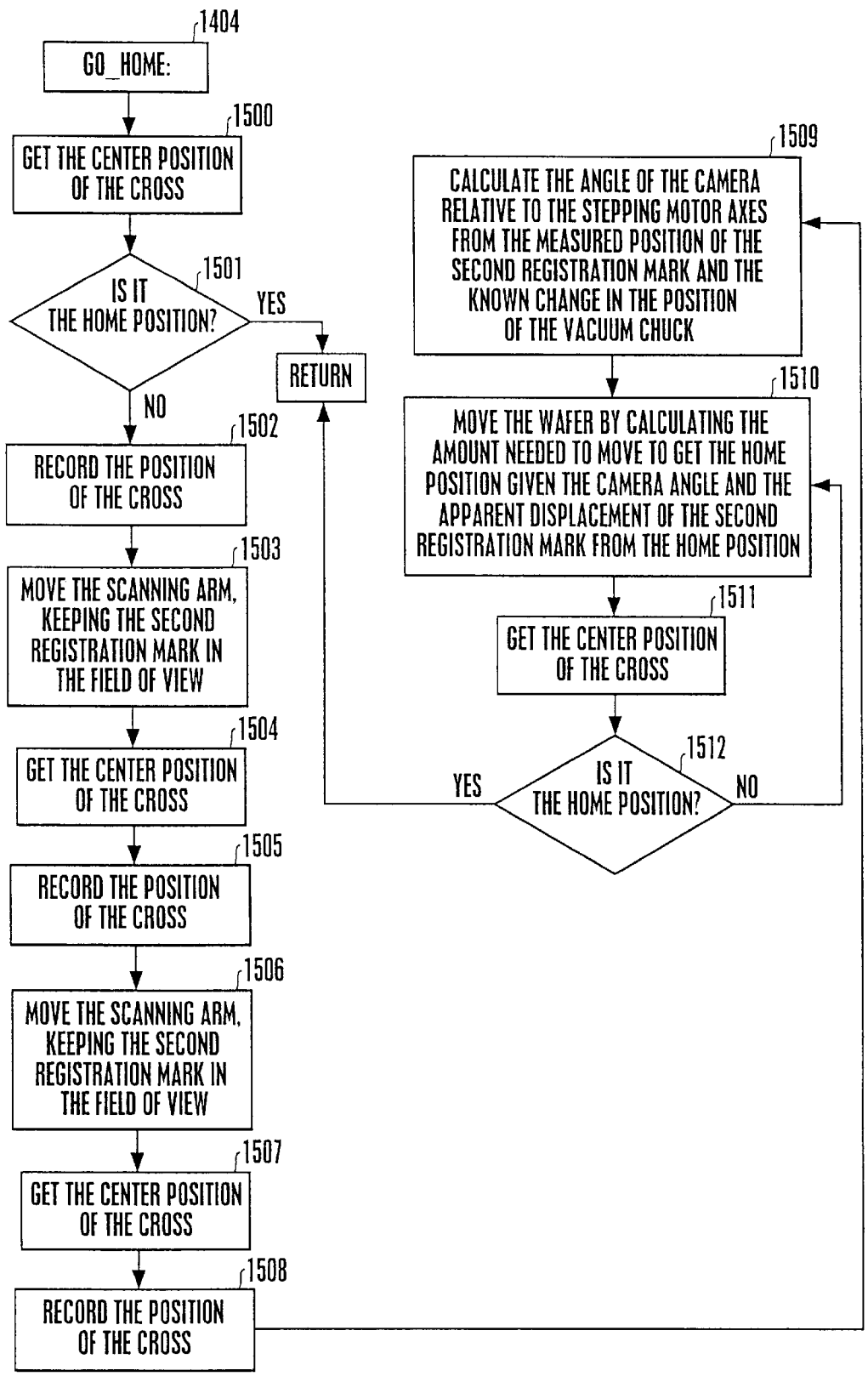
FIG. 17 is a flow chart depicting the operation of the software used to further align the substrate.

FIG. 17 shows the Go_home routine in detail. The program first checks whether the second registration mark is at the home position, i.e., being centered over the center of the camera (step 1501). If it is not, the position of the second registration mark is recorded and the scanning arm moves the wafer to two locations that leave the second registration mark in the field of view to measure how movements of the scanning arm cause the position of the second registration mark to vary the camera's frame of reference (steps 1502–1508). The program then calculates the angle of the camera relative to the stepping motor axes from the measured positions of the registration marks and the known change in position of the scanning arm (step 1509). The wafer is moved by calculating the amount needed to move the wafer to get to the home position given the camera angle and the apparent displacement of the second registration mark from the home position (step 1510). The program checks whether the wafer is at the home position (steps 1511–1512). If the wafer is not in the home position, the program repeats steps 1510–1512.

Figure 18:
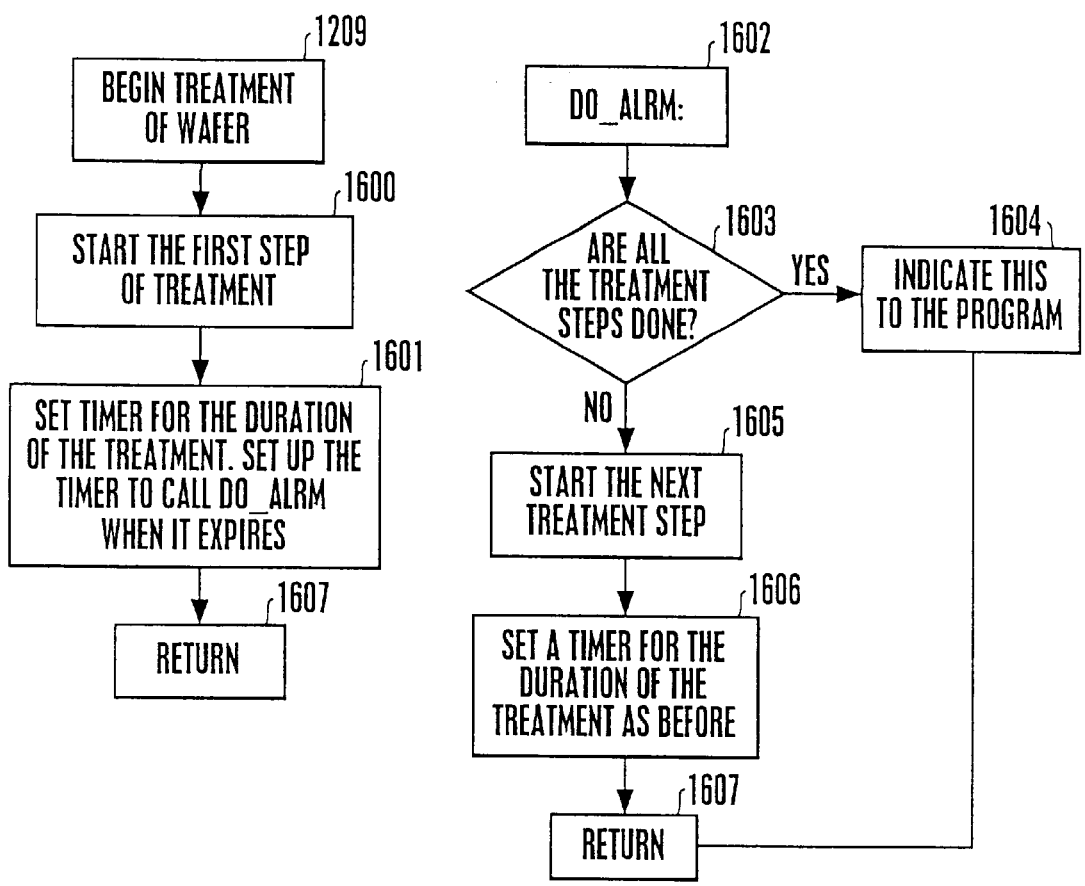
FIG. 18 is a flow chart depicting the operation of the software used to further control the operation of the flow cell.

FIG. 18 shows the routine for controlling the treatment in a flow cell, including rinsing and deprotection of a wafer. When the first step of treatment starts (step 1600), a timer is set for the duration of the treatment (step 1601). When the time expires, the timer calls the do_alrm routine which checks whether all the treatment steps are done (step 1603). If so, the do_alrm routine indicates this to the program (step 1604). If not, the next treatment is started (step 1605), and a timer is set for the duration of the treatment as before (step 1606).

Figure 19:
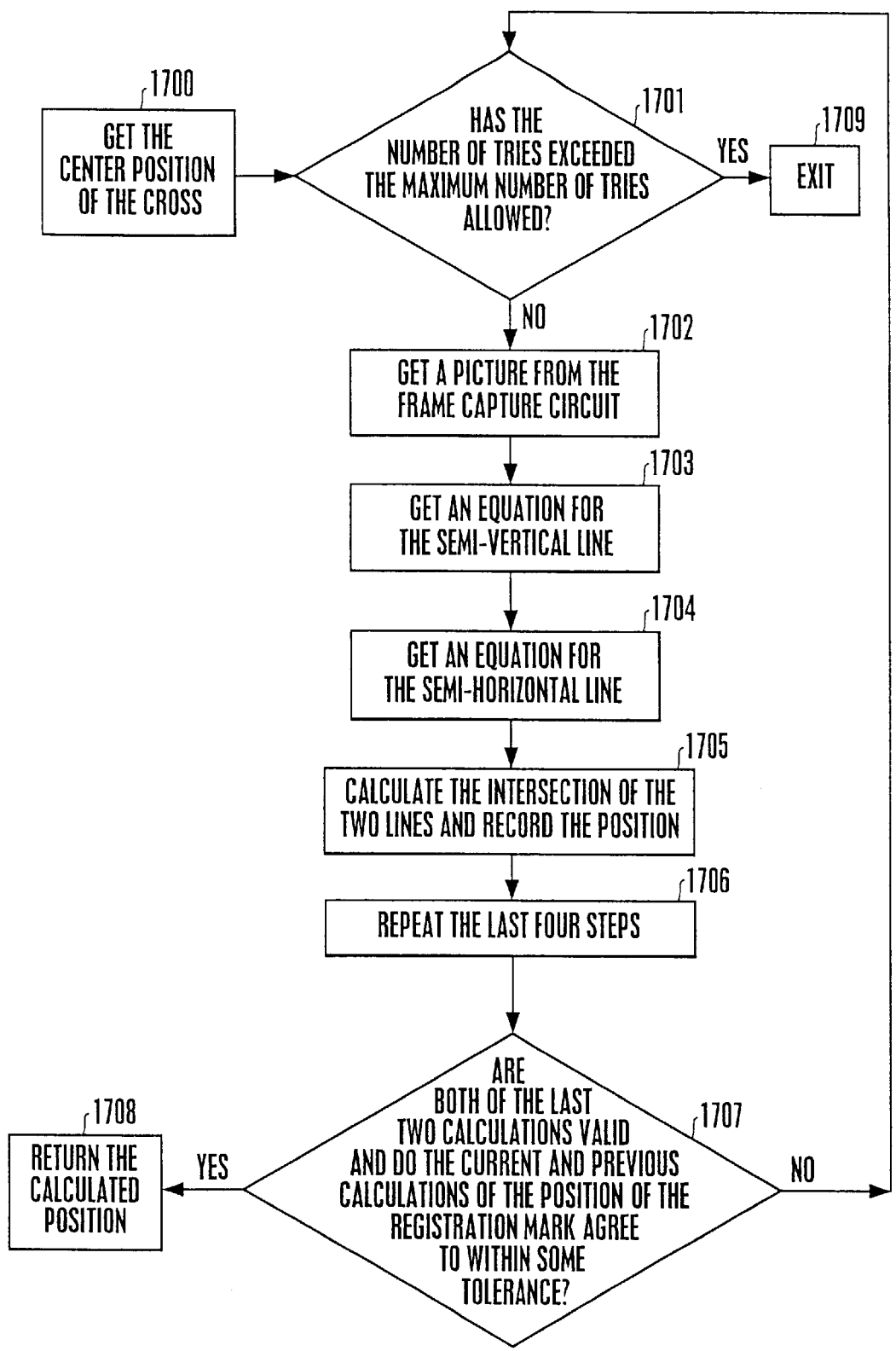
FIG. 19 is a flow chart depicting the operation of the software used to measure the center positions of registration marks used for alignment.

FIG. 19 shows in detail a routine for measuring the center position of the first or second registration mark. The program first obtains from the frame capture circuit a two-dimensional array of pixels of a digital image taken by the camera (step 1702). Typically, the registration mark will not be rotated more than one degree or so from its aligned position. A semi-vertical line and a semi-horizontal line can be identified from the array of pixels because one of the two lines in the registration mark will appear to be vertical and the other to be horizontal. The program calculates the equation for the semi-vertical line (step 1703). Similarly, the program calculates the equation for the semi-horizontal line (step 1704). The program then calculates the intersection of the two lines and records the position (step 1705). If the current and previous calculations of the position of the registration mark agree within some tolerance, the program returns the calculated position as the center position of the registration mark (steps 1707–1708). If they don't agree or any of the steps requires to estimate the position fails, the program re-tries at step 1701.

Figure 20:
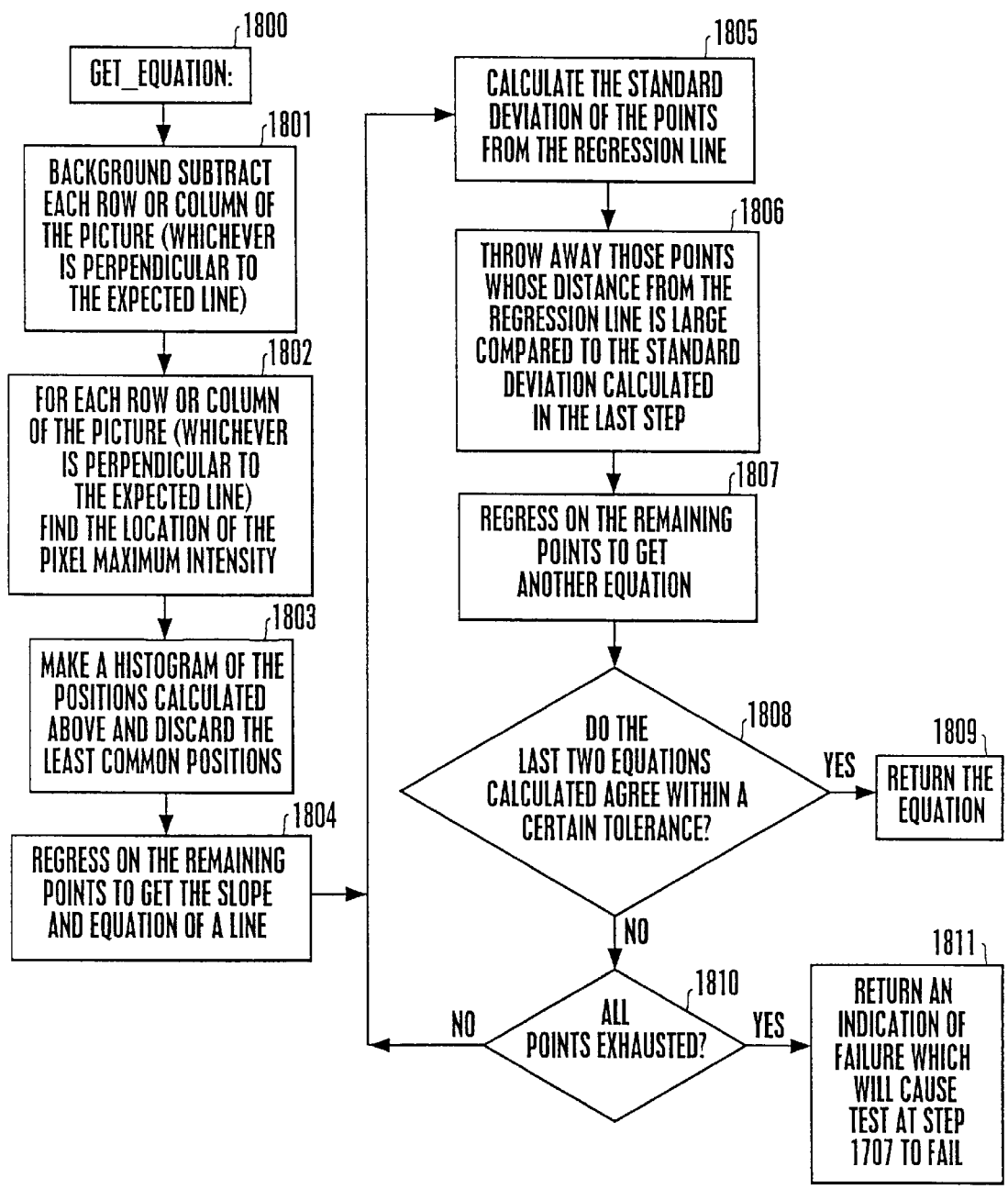
FIG. 20 is a flow chart depicting the operation of the software used to calculate the slope and equation of a line detected by a camera during alignment.

FIG. 20 shows in detail the programming steps for calculating the equation of the semi-vertical line or the semi-horizontal line. First, the pixel values are adjusted against the background (step 1801) by subtracting the background intensity from each pixel in order to compensate the effect of different lighting backgrounds. Then, for each row or column of the picture (whichever is perpendicular to the expected line), the program finds the location of the pixel of the maximum intensity (step 1802). The program makes a histogram of the positions calculated above and discards the positions below an occurrence frequency cutoff value (step 1803). The program performs a regression on the remaining points to get the equation for a line (step 1804). The program calculates the standard deviation of the points from the regression line (step 1805). The program throws away those points whose distance from the regression line is large compared to the standard deviation calculated in the last step (step 1806). The program performs a regression on the remaining points to get another equation. If the last two equations calculated agree within a certain tolerance, the program returns the equation (steps 1807–1809). The program continues the cycle of discarding points and regressing until either successive equations agree, or too few points remain.

Figure 21:
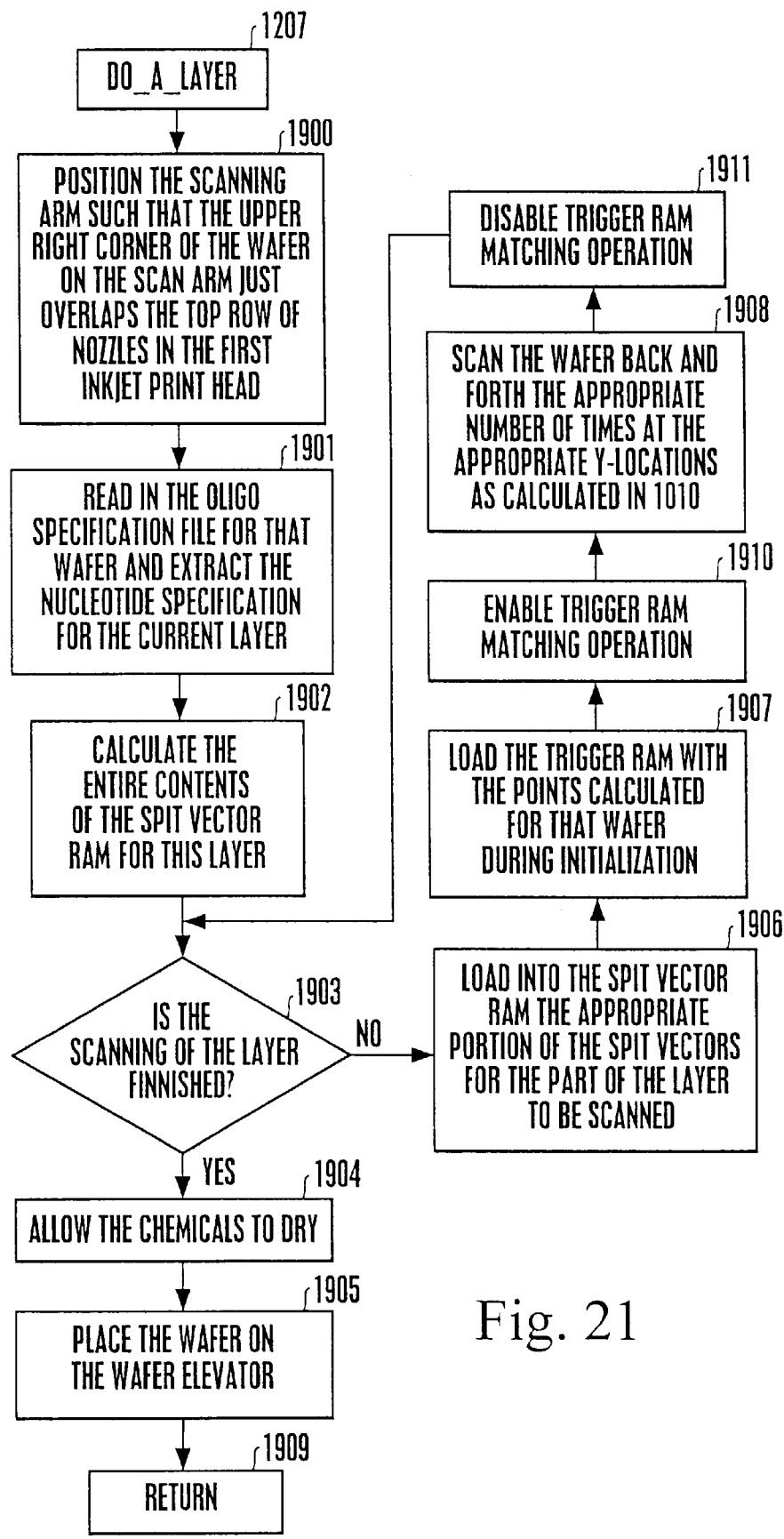
FIG. 21 is a flow chart depicting the operation of the software used control the deposition of a layer of nucleoside monomers.

FIG. 21 shows in detail the programming steps necessary for the Do_a_layer routine that controls the printer head and the scanning arm to deposit a particular layer. The scanning arm moves the wafer such that the upper right corner of the wafer just overlaps the top row of the nozzles in the first inkjet print head (step 1900). The program then reads in the oligo specification file containing the oligonucleotide sequences for the wafer and extracts the nucleoside specification for the current layer (step 1901). The program then calculates the entire contents of the spit vector RAM for this layer from the information obtained in previous steps (step 1902). The spit vector RAM contains spit vectors representing information of how to fire the array of nozzles at each trigger point (X-position).

Once the scanning (deposition) of the current layer has been done, the chemicals are allowed to dry and the wafer is placed on a wafer elevator (steps 1904–1905). If the scanning has not been done, the program loads into the spit vector RAM the appropriate portion of the spit vectors from step 1902 for the part of the next layer to scan. The program then loads the trigger RAM with the X-locations calculated for that wafer during the initialization (step 1907). The wafer is scanned back and forth the appropriate number of times at the appropriate Y-locations as calculated in step 1010 (step 1908).

EXAMPLE 1

Comparison of Result of Oligonucleotide Synthesis with Propylene Carbonate vs. Acetonitrile Solvent Nucleoside phosphoramidites used in this experiment are of the EXPEDITE type, and were obtained from Perseptive Biosystems, Framingham, Mass. The primary amino groups of the base portion of the adenosine (A), cytidine (C) and guanosine (G) nucleosides were protected with t-butylphenoxyacetyl (tBPA) groups. The 5'-hydroxyl groups of the A, C, G and thymidine (T) nucleosides were protected with a dimethoxytrityl (DMT) group. The 3'-hydroxyl groups of the A, C, G and T nucleosides were derivatized as β-cyanoethyl-N,N-diisopropylphosphoramidites.

This example compares the efficiency of nucleoside coupling when propylene carbonate is used as a reaction solvent, relative to that when acetonitrile is used, in conventional, solid phase nucleoside synthesis.

As shown below in Table 1, eight separate oligonucleotide homopolymers of A, T, C and G, each being eleven nucleotides in length, were assembled using either propylene carbonate or acetonitrile as the reaction solvent. Reagents were dispensed from an Applied Biosystems model 380B synthesizer, a non-inkjet synthesizer, using phosphoramidite chemistry according the manufacturer's instructions. A trityl assay (see T. Atkinson et al., *Solid-Phase Synthesis of Oligodeoxyribonucleotides by the Phosphite-Triester Method, in Oligonucleotide Synthesis* (M. J. Gait ed., 1984)) was used to estimate stepwise yields on all eight syntheses. This assay measures the amount of dimethoxytrityl group released during the deprotection step of the synthetic cycle. The measurement is conveniently carried out photometrically since the dimethoxytrityl group absorbs light strongly at 498 nm. Using this assay, an estimate of the efficiency of the synthetic reactions was made by comparing the amounts of dimethoxytrityl released from one cycle to the next. As shown in Table 1, yields of oligonucleotides that are obtained using either propylene carbonate or acetonitrile solvents, are comparable.

TABLE 1

Assembly of oligonucleotide homopolymers using acetonitrile or propylene carbonate

| % yield | polydT | | polydG | | polydA | | polydc | |
|---|---|---|---|---|---|---|---|---|
| | A* | PC | A | PC | A | PC | A | PC |
| Average | 99.4 | 99.6 | 99.3 | 97.4 | 97.8 | 96.6 | 98.9 | 98.4 |
| Overall | 88.8 | 89.4 | 87.6 | 74.1 | 77.6 | 65.9 | 88.8 | 85.4 |
| Stepwise | 98.8 | 98.9 | 98.7 | 97.0 | 97.5 | 95.9 | 98.8 | 98.4 |

*A = Acetonitrile;
PC = Propylene Carbonate

EXAMPLE 2

Synthesis of Two-Dimensional Oligonucleotide Arrays Using an Inkjet Print Head

This example describes the synthesis of a two-dimensional array of oligonucleotides using the synthesis system described in the section entitled System Implementation, above. With respect to the steps involving deposition of reagents using an inkjet printing head, i.e., those steps not involving oxidizing, rinsing, capping and deprotection, an earlier version of the software described in the section entitled Software Implementation, above, was used.

The nucleoside phosphoramidites used in this experiment were those described in Example 1, above.

An oxidizing solution, that was used to oxidize nucleoside phosphite triesters to nucleoside phosphate triesters, consisted of 90.54% (v/v) tetrahydrofuran, 9.05% (v/v) water, 0.41% (v/v) pyridine and 4.3 g/L iodine.

As mentioned before, inkjet print heads used herein were EPSON STYLUS COLOR II color heads, available from the manufacturer as spare parts, which consist of three banks of twenty nozzles each. All of the nozzles in each bank were connected to a common fluid intake manifold, such that each inkjet print head had three fluid lines connected thereto. The complete inkjet assembly consisted of two inkjet print heads mounted together, so as to form an assembly of six banks of twenty nozzles each.

Fifty clean, standard, glass microscope slides (25 mm×75 mm) were used as the substrates upon which the oligonucleotide arrays were assembled, and were derivatized according to the procedure of E. M. Southern et al., *Genomics* 13 (4):1008–1017 (1992). The slides were submerged in a bath of 200 mL of glycidoxypropyltrimethoxysilane, 800 mL of anhydrous xylenes and 10 mL of diisopropylethylamine for 8 h at 80° C. with stirring, and then rinsed with ethanol and dried under nitrogen. The resulting substrates were placed in a bath of 800 mL of tetraethylene glycol and 3 mL of conc. $H_2SO_4$ for 8 h at 80° C. with stirring, and then rinsed with ethanol and dried under nitrogen.

Four of the six inkjet banks of the assembly were loaded with 0.1 M solutions (propylene carbonate) of each nucleoside phosphoramidite and one of those six inkjet banks was loaded with a 0.5 M solution of 5-ethylthiotetrazole in propylene carbonate.

The derivatized substrate was affixed to an X-Y translation stage that was driven by two stepping motors via a lead screw. A computer, along with an appropriate electronic interface, was used to synchronize the firing of the inkjet print head with the motion of the X-Y translation stage, so as to deliver one 42 pL drop of the appropriate nucleoside phosphoramidite solution, followed by one 42 pL drop of the 5-ethylthiotetrazole solution to each region of the substrate where oligonucleotide synthesis was to take place. This reaction, which resulted in the coupling of each nucleoside to the substrate via a tetraethyleneglycol linker, was allowed to proceed for 60 seconds under a nitrogen atmosphere. The substrate was rinsed with acetonitrile to remove excess reagents, and dried with anhydrous nitrogen.

The resulting substrate was submerged in a bath of the oxidizing solution for 30 seconds so as to convert the resulting nucleoside phosphite triesters to nucleoside phosphate triesters. The substrate was then rinsed again with acetonitrile, and then treated with a solution of 20 pL of perfluorooctanoyl chloride in 50 mL of anhydrous xylene, so as to cap all of the unreacted hydroxyl groups of the tetraethylene glycol bonded to the substrate.

The resulting substrate was rinsed with acetonitrile, dried with anhydrous nitrogen, and then dipped for 60 seconds in a solution of 2.5% dichloroacetic acid in dichloromethane which removed the dimethoxytrityl protecting group from the 5'-hydroxyl group of nucleoside. After a final rinse with acetonitrile, and a drying stream of dry nitrogen, the substrate was subjected to 19 iterations of the (a) nucleoside coupling, (b) acetonitrile rinsing, (c) oxidation, (d) acetonitrile rinsing, (e) dimethoxytrityl deprotecting and (f) acetonitrile rinsing steps.

Finally, the substrate was dipped in undiluted ethanolamine for 20 minutes, at room temperature, to remove both the tBPA protecting groups from the nucleoside bases, and the cyanoethyl groups from the phosphate linkages between adjacent to nucleosides to provide phosphate groups. The substrate was then rinsed with ethanol, and then with acetonitrile, leaving the resulting oligonucleotide attached to the substrate.

The present invention is not to be limited in scope by the specific embodiments disclosed in the examples which are intended as illustrations of a few aspects of the invention, and any embodiments which are functionally equivalent are within the scope of this invention. Indeed, various modifications of the invention, in addition to those shown and described herein, will become apparent to those skilled in the art, and are intended to fall within the appended claims.

A number of references have been cited, and the entire disclosures of which are incorporated herein by reference.

What is claimed is:

1. An inkjet print head comprising a piezoelectric pump, wherein said print head contains a solvent having a boiling point of 150° C. or above, a surface tension of 30 dynes/cm or above, and a viscosity of 0.015 g/(cm)(sec) or above, which inkjet printhead does not contain a solvent having a hydroxyl group.

2. The inkjet print head of claim 1, wherein the solvent has the formula (I):

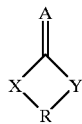

(I)

wherein
  A=O or S;
  X=O, S or N(C$_1$–C$_4$ alkyl);
  Y=O, S, N(C$_1$–C$_4$ alkyl) or CH$_2$; and
  R=C$_2$–C$_{20}$ straight or branched chain alkyl.

3. The inkjet print head of claim 2, wherein said solvent is selected from the group consisting of:
  N-methyl-2-pyrrolidine;
  2-pyrrolidine;
  propylene carbonate;
  γ-valerolactone;
  6-caprolactam;
  ethylene carbonate;
  γ-butyrolactone;
  δ-valerolactone;
  1,3-dimethyl-3,4,5,6-tetrahydro-2(1H)-pyrimidinone;
  ethylene trithiocarbonate; and
  1,3-dimethyl-2-imidazolidinone.

4. The inkjet print head of claim 3, wherein the solvent is propylene carbonate.

5. The inkjet print head of claim 1, which does not contain a solvent having a primary or secondary amino group.

6. The inkjet print head of claim 1, which does not contain a solvent having a sulfhydryl group.

7. The inkjet print head of claim 1, which does not contain a solvent having a carboxyl group.

8. The inkjet print head of claim 1, which does not contain a solvent having an anhydride group.

9. An inkjet print head containing a solution comprising a solvent having a boiling point of 150° C. or above, a surface tension of 30 dynes/cm or above, and a viscosity of 0.015 g/(cm)(sec) or above, and a nucleoside or an activated nucleoside.

10. The inkjet print head of claim 9, wherein the solvent has the formula (I):

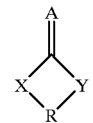

(I)

wherein
  A=O or S;
  X=O, S or N(C$_1$–C$_4$ alkyl);
  Y=O, S, N(C$_1$–C$_4$ alkyl) or CH$_2$; and
  R=C$_2$–C$_{20}$ straight or branched chain alkyl.

11. The inkjet print head of claim 10, wherein the solvent is selected from the group consisting of:
  N-methyl-2-pyrrolidone;
  2-pyrrolidone;
  propylene carbonate;
  γ-valerolactone;
  6-caprolactam;
  ethylene carbonate;
  γ-butyrolactone;
  δ-valerolactone;
  1,3-dimethyl-3,4,5,6-tetrahydro-2(1H)-pyrimidinone;
  ethylene trithiocarbonate; and
  1,3-dimethyl-2-imidazolidinone.

12. The inkjet print head of claim 11, wherein the solvent is propylene carbonate.

13. An inkjet print head containing a solution comprising propylene carbonate and a nucleoside having a phosphodiester, phosphotriester, phosphate triester, H-phosphonate or phosphoramidite group.

14. An inkjet print head containing a solution comprising a solvent having a boiling point of 150° C. or above, a surface tension of 30 dynes/cm or above, and a viscosity of 0.015 g/(cm)(sec) or above, and an amino acid.

15. The inkjet print head of claim 14, wherein the solvent has the formula (I):

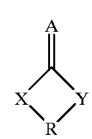

(I)

wherein
  A=O or S;
  X=O, S or N(C$_1$–C$_4$ alkyl);
  Y=O, S, N(C$_1$–C$_4$ alkyl) or CH$_2$; and
  R=C$_2$–C$_{20}$ straight or branched chain alkyl.

16. The inkjet print head of claim 15, wherein the solvent is selected from the group consisting of:
  N-methyl-2-pyrrolidone;
  2-pyrrolidone;
  propylene carbonate;
  γ-valerolactone;
  6-caprolactam;
  ethylene carbonate;
  γ-butyrolactone;
  δ-valerolactone;

1,3-dimethyl-3,4,5,6-tetrahydro-2(1H)-pyrimidinone;
ethylene trithiocarbonate; and
1,3-dimethyl-2-imidazolidinone.

17. The inkjet print head of claim 16, wherein the solvent is propylene carbonate.

18. An inkjet print head containing a solution comprising a solvent having a boiling point of 150° C. or above, a surface tension of 30 dynes/cm or above, and a viscosity of 0.015 g/(cm)(sec) or above, and a catalyst, which inkjet printhead does not contain a solvent having a hydroxyl group.

19. The inkjet print head of claim 18, wherein the solvent has the formula (I):

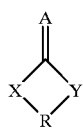

(I)

wherein
A=O or S;
X=O, S or N($C_1$–$C_4$ alkyl);
Y=O, S, N($C_1$–$C_4$ alkyl) or $CH_2$; and
R=$C_2$–$C_{20}$ straight or branched chain alkyl.

20. The inkjet print head of claim 19, wherein the solvent is selected from the group consisting of:
N-methyl-2-pyrrolidone;
2-pyrrolidone;
propylene carbonate;
γ-valerolactone;
6-caprolactam;
ethylene carbonate;
γ-butyrolactone;
δ-valerolactone;
1,3-dimethyl-3,4,5,6-tetrahydro-2(1H)-pyrimidinone;
ethylene trithiocarbonate; and
1,3-dimethyl-2-imidazolidinone.

21. The inkjet print head of claim 20, wherein the solvent is propylene carbonate.

22. The inkjet print head of any of claims 18–21, wherein said catalyst is selected from the group consisting of 5-methylthiotetrazole, tetrazole, 5-ethylthiotetrazole and dicyclohexylcarbodiimide.

23. An inkjet print head containing a solution comprising a solvent having a boiling point of 150° C. or above, a surface tension of 30 dynes/cm or above, and a viscosity of 0.015 g/(cm)(sec) or above, and a catalyst, wherein said catalyst is selected from the group consisting of 5-methylthiotetrazole, tetrazole, 5-ethylthiotetrazole and dicyclohexylcarbodiimide.

24. The inkjet print head of claim 23, wherein the solvent has the formula (I):

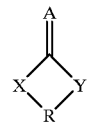

(I)

wherein
A=O or S;
X=O, S or N($C_1$–$C_4$ alkyl);
Y=O, S, N($C_1$–$C_4$ alkyl) or $CH_2$; and
R=$C_2$–$C_{20}$ straight or branched chain alkyl.

25. The inkjet print head of claim 24, wherein the solvent is selected from the group consisting of:
N-methyl-2-pyrrolidone;
2-pyrrolidone;
propylene carbonate;
γ-valerolactone;
6-caprolactam;
ethylene carbonate;
γ-butyrolactone;
δ-valerolactone;
1,3-dimethyl-3,4,5,6-tetrahydro-2(1H)-pyrimidinone;
ethylene trithiocarbonate; and
1,3-dimethyl-2-imidazolidinone.

26. The inkjet print head of claim 25, wherein the solvent is propylene carbonate.

27. An inkjet print head containing a solvent selected from the group consisting of:
2-pyrrolidone;
propylene carbonate;
γ-valerolactone;
6-caprolactam;
ethylene carbonate;
γ-butyrolactone;
δ-valerolactone;
1,3-dimethyl-3,4,5,6-tetrahydro-2(1H)-pyrimidinone;
ethylene trithiocarbonate; and
1,3-dimethyl-2-imidazolidinone,
which inkjet printhead does not contain a solvent having a hydroxyl group.

28. An inkjet print head containing propylene carbonate, which inkjet printhead does not contain a solvent having a hydroxyl group.

* * * * *